(12) United States Patent
Toledano et al.

(10) Patent No.: US 12,350,382 B2
(45) Date of Patent: *Jul. 8, 2025

(54) METHOD FOR PREPARING PARTICLES COMPRISING METAL OXIDE COATING AND PARTICLES WITH METAL OXIDE COATING

(75) Inventors: Ofer Toledano, Kfar Saba (IL); Haim Bar-Simantov, Netanya (IL); Nissim Bilman, Rehovot (IL); Leora Shapiro, Jerusalem (IL); Raed Abu-Reziq, Jatt Hamesholash (IL); Srikanth Sriadibhatla, Parisppany, NJ (US); William T. Sommer, Mendham, NJ (US); Hanan Sertchook, Gedera (IL)

(73) Assignee: Mayne Pharma LLC, Raleigh, NC (US)

( * ) Notice: Subject to any disclaimer, the term of this patent is extended or adjusted under 35 U.S.C. 154(b) by 173 days.

This patent is subject to a terminal disclaimer.

(21) Appl. No.: 12/525,331

(22) PCT Filed: Feb. 3, 2008

(86) PCT No.: PCT/IL2008/000141
§ 371 (c)(1),
(2), (4) Date: Oct. 6, 2009

(87) PCT Pub. No.: WO2008/093347
PCT Pub. Date: Aug. 7, 2008

(65) Prior Publication Data
US 2010/0016443 A1    Jan. 21, 2010

Related U.S. Application Data

(60) Provisional application No. 60/898,700, filed on Feb. 1, 2007.

(51) Int. Cl.
| | | |
|---|---|---|
| *A61K 9/50* | (2006.01) | |
| *A01N 25/26* | (2006.01) | |
| *A01N 53/00* | (2006.01) | |
| *A61K 8/11* | (2006.01) | |
| *A61K 8/25* | (2006.01) | |
| *A61K 8/38* | (2006.01) | |
| *A61K 8/67* | (2006.01) | |
| *A61Q 19/00* | (2006.01) | |
| *B01J 13/02* | (2006.01) | |
| *B01J 13/22* | (2006.01) | |
| *C09C 3/06* | (2006.01) | |

(52) U.S. Cl.
CPC .......... *A61K 9/5073* (2013.01); *A01N 25/26* (2013.01); *A01N 53/00* (2013.01); *A61K 8/11* (2013.01); *A61K 8/25* (2013.01); *A61K 8/38* (2013.01); *A61K 8/671* (2013.01); *A61Q 19/00* (2013.01); *B01J 13/02* (2013.01); *B01J 13/22* (2013.01); *C09C 3/063* (2013.01); *A61K 9/501* (2013.01); *A61K 9/5021* (2013.01); *A61K 9/5026* (2013.01); *A61K 2800/412* (2013.01); *Y10T 428/2991* (2015.01)

(58) Field of Classification Search
CPC .......... A61K 9/5073; A61K 8/11; A61K 8/25; A61K 8/38; A61K 8/671; A61K 9/501; A61K 9/5021; A61K 9/5026; A61K 2800/412; A61K 8/02; A61K 9/00; A01N 25/26; A01N 53/00; A61Q 19/00; B01J 13/02; B01J 13/22; C09C 3/063; Y10T 428/2991; A61P 17/00; A61P 17/06; A61P 17/10; A61P 17/04; A61P 17/08
See application file for complete search history.

(56) References Cited

U.S. PATENT DOCUMENTS

| | | |
|---|---|---|
| 1,387,107 A | 8/1921 | Carr |
| 1,671,956 A | 5/1928 | Sime |
| 2,885,366 A | 5/1959 | Iler |

(Continued)

FOREIGN PATENT DOCUMENTS

| | | |
|---|---|---|
| AU | 199963469 B2 | 5/2000 |
| AU | 2002364437 A1 | 7/2003 |

(Continued)

OTHER PUBLICATIONS

Skapin et al. Journal of Colloid and Interface Science. 2004; 272: 90-98.*

(Continued)

*Primary Examiner* — David Browe
(74) *Attorney, Agent, or Firm* — Mark S. Cohen; PEARL COHEN ZEDEK LATZER BARATZ LLP

(57) ABSTRACT

The invention relates to a process for coating a solid, water-insoluble particulate matter, with a metal oxide comprising: (a) contacting the solid, water-insoluble particulate matter with an ionic additive and an aqueous medium to obtain a dispersion of said particulate matter having positive charges on its surface; (b) subjecting the particulate matter to a coating procedure comprising precipitating a metal oxide salt onto the surface of the particulate matter to form a metal oxide layer thereon to thereby obtain particulate matter coated by a metal oxide coating layer; (c) repeating step (b) at least 4 more times; and (d) aging said coating layer. The invention further relates to particles comprising a particulate matter coated by a metal oxide layer, to a use of the particles for topical administration, and to a method for preventing, reducing, or eliminating pests at a locus, using the particles.

11 Claims, 1 Drawing Sheet

(56) References Cited

U.S. PATENT DOCUMENTS

Figure 1:
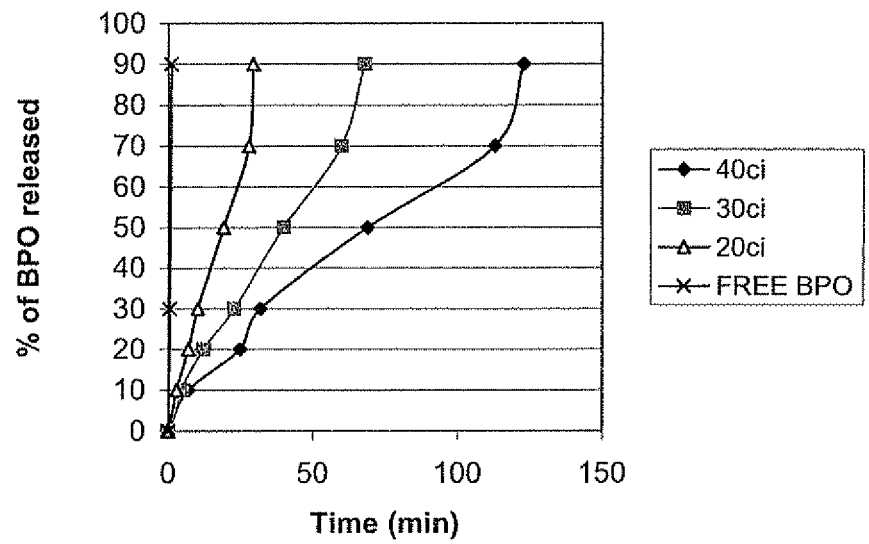

| | | |
|---|---|---|
| 3,785,798 A | 1/1974 | Horai et al. |
| 3,826,670 A | 7/1974 | Rees |
| 3,957,971 A | 5/1976 | Oleniacz |
| 4,129,645 A | 12/1978 | Barnett et al. |
| 4,169,069 A | 9/1979 | Unger et al. |
| 4,349,456 A | 9/1982 | Sowman |
| 4,350,681 A | 9/1982 | Fulton, Jr. |
| 4,361,584 A | 11/1982 | Fulton, Jr. |
| 4,387,107 A | 6/1983 | Klein et al. |
| 4,444,746 A | 4/1984 | Harvey et al. |
| 4,464,317 A | 8/1984 | Thies et al. |
| 4,497,794 A | 2/1985 | Klein et al. |
| 4,606,913 A | 8/1986 | Aronson et al. |
| 4,671,956 A | 6/1987 | Bouillon et al. |
| 4,686,211 A | 8/1987 | Hara et al. |
| 4,690,825 A | 9/1987 | Won |
| 4,692,329 A | 9/1987 | Klein et al. |
| 4,769,080 A | 9/1988 | Clark et al. |
| 4,891,211 A | 1/1990 | Winston |
| 4,931,362 A | 6/1990 | Zsifkovits et al. |
| 4,960,772 A | 10/1990 | Sebag et al. |
| 4,988,744 A | 1/1991 | Yamamoto |
| 5,086,075 A | 2/1992 | De Villez |
| 5,126,915 A * | 6/1992 | Pepin et al. .................. 361/304 |
| 5,145,675 A | 9/1992 | Won |
| 5,165,914 A | 11/1992 | Vlock |
| 5,185,155 A | 2/1993 | Behan et al. |
| 5,200,334 A | 4/1993 | Dunn et al. |
| 5,223,250 A | 6/1993 | Mitchell et al. |
| 5,269,840 A | 12/1993 | Morris et al. |
| 5,292,801 A | 3/1994 | Avnir et al. |
| 5,318,797 A | 7/1994 | Matijevic et al. |
| 5,387,622 A | 2/1995 | Yamamoto |
| 5,401,517 A | 3/1995 | Meyers et al. |
| 5,446,028 A | 8/1995 | Klein et al. |
| 5,455,048 A | 10/1995 | Lahmani et al. |
| 5,466,446 A | 11/1995 | Stiefel et al. |
| 5,468,471 A | 11/1995 | Zecchino et al. |
| 5,472,491 A | 12/1995 | Duschek et al. |
| 5,500,223 A | 3/1996 | Behan et al. |
| 5,520,917 A | 5/1996 | Mizuguchi et al. |
| 5,556,617 A | 11/1996 | Ribier et al. |
| 5,587,170 A | 12/1996 | Caisey et al. |
| 5,591,453 A | 1/1997 | Ducheyne et al. |
| 5,607,664 A | 3/1997 | Ascione et al. |
| 5,632,996 A | 5/1997 | Ramirez et al. |
| 5,635,609 A | 6/1997 | Levy et al. |
| 5,635,809 A | 6/1997 | Ganser et al. |
| 5,650,311 A | 7/1997 | Avnir et al. |
| 5,670,209 A | 11/1997 | Wyckoff |
| 5,672,301 A | 11/1997 | Orly et al. |
| 5,691,060 A | 11/1997 | Levy |
| 5,700,451 A | 12/1997 | Yue et al. |
| 5,733,531 A | 3/1998 | Mitchnick et al. |
| 5,739,020 A | 4/1998 | Pope |
| 5,767,098 A | 6/1998 | Klein et al. |
| 5,785,977 A | 7/1998 | Breithbarth |
| 5,792,250 A | 8/1998 | Braun et al. |
| 5,851,538 A | 12/1998 | Froix et al. |
| 5,874,105 A | 2/1999 | Watkins et al. |
| 5,876,699 A | 3/1999 | DiSomma et al. |
| 5,879,716 A | 3/1999 | Katz et al. |
| 5,895,757 A | 4/1999 | Pope |
| 5,906,811 A | 5/1999 | Hersh |
| 5,912,016 A | 6/1999 | Perrier et al. |
| 5,914,101 A | 6/1999 | Tapley et al. |
| 5,914,104 A | 6/1999 | Moore, Jr. |
| 5,914,116 A | 6/1999 | Suares et al. |
| 5,932,288 A | 8/1999 | Hall et al. |
| 5,955,109 A | 9/1999 | Won et al. |
| 5,962,517 A | 10/1999 | Murad |
| 5,998,392 A | 12/1999 | Simard et al. |
| 6,013,637 A | 1/2000 | Klein et al. |
| 6,015,548 A | 1/2000 | Siddiqui et al. |
| 6,074,629 A | 6/2000 | Kostinko et al. |
| 6,077,522 A | 6/2000 | Scher et al. |
| 6,090,399 A | 7/2000 | Ghosh et al. |
| 6,096,765 A | 8/2000 | Bershad |
| 6,103,267 A | 8/2000 | Mitchnick et al. |
| 6,117,843 A | 9/2000 | Baroody et al. |
| 6,132,773 A | 10/2000 | Amiche |
| 6,143,280 A | 11/2000 | Pike et al. |
| 6,146,664 A | 11/2000 | Siddiqui |
| 6,159,453 A | 12/2000 | Avnir et al. |
| 6,171,600 B1 | 1/2001 | Dahms |
| 6,197,757 B1 | 3/2001 | Perrier et al. |
| 6,200,375 B1 | 3/2001 | Guez et al. |
| 6,217,852 B1 | 4/2001 | Gildenberg et al. |
| 6,238,650 B1 | 5/2001 | Lapidot et al. |
| 6,242,099 B1 | 6/2001 | Grandmontagne et al. |
| 6,251,313 B1 | 6/2001 | Deubzer et al. |
| 6,280,746 B1 | 8/2001 | Arquette et al. |
| 6,303,149 B1 | 10/2001 | Magdassi et al. |
| 6,303,290 B1 | 10/2001 | Liu et al. |
| 6,337,089 B1 | 1/2002 | Yoshioka et al. |
| 6,436,375 B1 | 8/2002 | Lapidot et al. |
| 6,468,509 B2 | 10/2002 | Lapidot et al. |
| 6,479,146 B1 | 11/2002 | Caruso et al. |
| 6,495,352 B1 | 12/2002 | Brinker et al. |
| 6,534,044 B1 * | 3/2003 | Wada et al. .................... 424/59 |
| 6,537,583 B1 | 3/2003 | Dupuis et al. |
| 6,607,713 B1 | 8/2003 | Chodorowski et al. |
| 6,616,947 B1 | 9/2003 | Depuis |
| 6,703,032 B2 | 3/2004 | Gers-Barlag et al. |
| 6,855,335 B2 | 2/2005 | Seok et al. |
| 6,875,264 B2 | 4/2005 | Zimmermann et al. |
| 6,913,825 B2 * | 7/2005 | Ostafin et al. ............... 428/402 |
| 6,939,552 B2 | 9/2005 | Ansara et al. |
| 7,001,592 B2 | 2/2006 | Traynor et al. |
| 7,037,513 B1 | 5/2006 | Traynor et al. |
| 7,052,913 B2 | 5/2006 | Babich et al. |
| 7,758,888 B2 | 6/2010 | Lapidot et al. |
| 8,039,020 B2 | 10/2011 | Lapidot et al. |
| 8,449,918 B2 | 5/2013 | Lapidot et al. |
| 8,568,704 B2 | 10/2013 | Mallard et al. |
| 9,687,465 B2 | 6/2017 | Sertchook et al. |
| 9,868,103 B2 | 1/2018 | Toledano et al. |
| 2002/0064541 A1 * | 5/2002 | Lapidot .................. A61P 3/02 424/401 |
| 2002/0144192 A1 | 10/2002 | Owari |
| 2002/0151527 A1 | 10/2002 | Wiegand et al. |
| 2002/0187197 A1 | 12/2002 | Caruso et al. |
| 2002/0193321 A1 | 12/2002 | Vishnupad et al. |
| 2003/0004118 A1 | 1/2003 | Wishnupad et al. |
| 2003/0082217 A1 | 5/2003 | Afriat et al. |
| 2003/0157330 A1 * | 8/2003 | Ostafin et al. ............... 428/404 |
| 2003/0170196 A1 | 9/2003 | Orsoni et al. |
| 2004/0096419 A1 | 5/2004 | Golz-Berner et al. |
| 2004/0101566 A1 | 5/2004 | Cooper et al. |
| 2004/0157766 A1 | 8/2004 | Embil et al. |
| 2005/0037087 A1 | 2/2005 | Lapidot et al. |
| 2005/0133036 A1 | 6/2005 | Steindorf |
| 2005/0208134 A1 | 9/2005 | Magdassi et al. |
| 2005/0276807 A1 | 12/2005 | Skurkovich et al. |
| 2006/0014834 A1 | 1/2006 | Vishnupad et al. |
| 2006/0128808 A1 | 6/2006 | Arsonnaud et al. |
| 2006/0167138 A1 | 7/2006 | Ishil et al. |
| 2006/0204530 A1 | 9/2006 | Ramirez et al. |
| 2006/0251687 A1 | 11/2006 | Lapidot et al. |
| 2006/0292093 A1 | 12/2006 | Carola et al. |
| 2007/0003585 A1 | 1/2007 | Clark et al. |
| 2007/0292676 A1 | 12/2007 | Naigertsik et al. |
| 2008/0292560 A1 | 11/2008 | Tamarkin et al. |
| 2009/0081262 A1 | 3/2009 | Toledano et al. |
| 2009/0304820 A1 | 12/2009 | Modi |
| 2010/0016443 A1 | 1/2010 | Toledano et al. |
| 2010/0047357 A1 | 2/2010 | Toledano et al. |
| 2010/0143285 A1 | 6/2010 | Mallard et al. |
| 2010/0203121 A1 | 8/2010 | Toledano et al. |
| 2011/0045037 A1 | 2/2011 | Tamarkin et al. |
| 2011/0052515 A1 | 3/2011 | Kaoukhov et al. |
| 2011/0177951 A1 | 7/2011 | Toledano et al. |
| 2011/0237555 A1 | 9/2011 | Sánchez et al. |
| 2011/0262506 A1 | 10/2011 | Toledano et al. |

(56) References Cited

U.S. PATENT DOCUMENTS

| | | |
|---|---|---|
| 2012/0015014 A1 | 1/2012 | Lapidot et al. |
| 2012/0064135 A1 | 3/2012 | Levin et al. |
| 2012/0202695 A1 | 8/2012 | Toledano et al. |
| 2012/0269874 A1 | 10/2012 | Toledano et al. |
| 2013/0095185 A1 | 4/2013 | Toledano et al. |
| 2014/0147396 A1 | 5/2014 | Sertchook et al. |
| 2017/0281571 A1 | 10/2017 | Sertchook et al. |
| 2018/0101284 A1 | 4/2018 | Pope et al. |
| 2018/0147165 A1 | 5/2018 | Sertchook et al. |
| 2018/0207451 A1 | 7/2018 | Toledano et al. |
| 2018/0339176 A1 | 11/2018 | Toledano et al. |

FOREIGN PATENT DOCUMENTS

| | | |
|---|---|---|
| AU | 764016 | 8/2003 |
| AU | 2008246274 B2 | 12/2008 |
| CN | 1290911 C | 12/2006 |
| CN | 101605537 A | 12/2009 |
| DE | 44 16 003 A1 | 11/1995 |
| DE | 19811900 A1 | 9/1999 |
| DE | 202011100767 U1 | 12/2011 |
| EP | 0 281 034 A2 | 2/1988 |
| EP | 0 462 388 A2 | 5/1991 |
| EP | 0 478 326 A1 | 9/1991 |
| EP | 0 581 651 A2 | 2/1994 |
| EP | 0680753 A2 | 11/1995 |
| EP | 0 934 773 A2 | 8/1999 |
| EP | 0 941 761 A2 | 9/1999 |
| EP | 0972563 A1 | 1/2000 |
| EP | 1 116 516 A1 | 7/2001 |
| EP | 1 511 802 B1 | 3/2005 |
| FR | 2 703 927 | 10/1994 |
| FR | 2 774 906 A1 | 8/1999 |
| FR | 2 780 901 | 1/2000 |
| FR | 2 833 841 | 6/2003 |
| GB | 1 399 344 | 7/1975 |
| GB | 2 088 717 A | 6/1982 |
| GB | 2 416 524 A | 2/2006 |
| JP | A-1-113436 | 5/1989 |
| JP | A-02-002867 | 1/1990 |
| JP | 02-417623 | 2/1990 |
| JP | A-2-40302 | 2/1990 |
| JP | A-02-251240 | 10/1990 |
| JP | A-02-292824 | 12/1990 |
| JP | A-3-229634 | 10/1991 |
| JP | A-03-243663 | 10/1991 |
| JP | A-05-043208 | 2/1993 |
| JP | A-07-173452 | 7/1995 |
| JP | A-09-110463 | 4/1997 |
| JP | A-09-235217 | 9/1997 |
| JP | A-2003-534249 | 11/2003 |
| JP | A-2005-513146 | 5/2005 |
| JP | A-2005-528152 | 9/2005 |
| JP | A-2005-529636 | 10/2005 |
| RU | 98105780 A | 12/1999 |
| RU | 2314093 C2 | 1/2008 |
| WO | WO 94/04260 | 3/1994 |
| WO | WO 94/04261 | 3/1994 |
| WO | WO 97/07676 A1 | 3/1997 |
| WO | WO 97/32561 | 9/1997 |
| WO | WO 97/40106 | 10/1997 |
| WO | WO 97/45367 | 12/1997 |
| WO | WO 98/15183 A1 | 4/1998 |
| WO | WO 98/31333 A1 | 7/1998 |
| WO | WO 99/03450 | 1/1999 |
| WO | WO 99/47253 | 9/1999 |
| WO | WO 00/09652 A2 | 2/2000 |
| WO | WO 00/25761 A1 | 5/2000 |
| WO | WO 00/25908 | 5/2000 |
| WO | WO 00/47236 | 8/2000 |
| WO | WO 00/71084 A1 | 11/2000 |
| WO | WO 00/72806 A2 | 12/2000 |
| WO | WO 01/12221 A1 | 2/2001 |
| WO | WO 01/13924 A1 | 3/2001 |
| WO | WO 01/58451 A1 | 8/2001 |
| WO | WO 01/80823 A2 | 11/2001 |
| WO | WO 02/085113 A1 | 10/2002 |
| WO | WO 03/003497 A | 1/2003 |
| WO | WO 03/034973 A1 | 5/2003 |
| WO | WO 03/039510 A1 | 5/2003 |
| WO | WO-2003034979 A2 | 5/2003 |
| WO | WO 03/066209 A1 | 8/2003 |
| WO | WO 03/086419 A | 10/2003 |
| WO | WO 03/099295 A | 12/2003 |
| WO | WO 03/104319 A1 | 12/2003 |
| WO | WO 2004/064769 A2 | 8/2004 |
| WO | WO 2004/064803 | 8/2004 |
| WO | WO 2004/069135 A2 | 8/2004 |
| WO | WO 2004/069216 A1 | 8/2004 |
| WO | WO 2004/081222 A2 | 9/2004 |
| WO | WO 2005/009604 A1 | 2/2005 |
| WO | WO 2007/000316 A1 | 1/2007 |
| WO | 2007015243 A2 | 2/2007 |
| WO | WO 2007/015243 | 2/2007 |
| WO | WO 2007/036939 A2 | 4/2007 |
| WO | WO 2008/002637 A2 | 1/2008 |
| WO | WO-2008057411 A1 | 5/2008 |
| WO | WO-2008065306 A1 | 6/2008 |
| WO | WO 2008/093346 A2 | 8/2008 |
| WO | WO 2008/093347 A2 | 8/2008 |
| WO | WO 2009/148584 A1 | 12/2009 |
| WO | WO 2010/013250 A1 | 2/2010 |
| WO | WO 2011/049547 A1 | 4/2011 |
| WO | 2012037000 A1 | 3/2012 |

OTHER PUBLICATIONS

Tjandra et al. Langmuir. 2006; 22: 1493-1499.*
He et al. Chem Mater. 2003; 15: 3308-3313.*
Bartlett et al. J Am Chem Soc. 1947; 69: 2299-2306. (Year: 1947).*
Villalobos et al., "Protective Silica Coatings on Zinc-Sulfide-Based Phosphor Particles", Journal of the American Ceramic Society, 2002, vol. 85, No. 8, pp. 2128-2130.
Wang et al., "Effect of Polyelectrolyte Dispersants on the Preparation of Silica-Coated Zinc Oxide Particles in Aqueous Media", Journal of the American Ceramic Society, 2002, vol. 85, No. 8, pp. 1937-1940.
Wilhelm et al., "On-line tracking of the coating of nanoscaled silica with titania nanoparticles via zeta-potential measurements", Journal of Colloid and Interface Science, 2006, vol. 293, pp. 88-92.
Makarova et al., "Adsorption and Encapsulation of Fluorescent Probes in Nanoparticles", J. Phys. Chem. B, American Chemical Society, 1999, vol. 103, No. 43, pp. 9080-9084.
Martindale, XP-002477043, 1999, pp. 1093-1095.
Merikhi et al., "Adhesion of Colloidal $SiO_2$ Particles on ZnS-Type Phosphor Surfaces", Journal of Colloid and Interface Science, 2000, vol. 228, pp. 121-126.
Mikrajuddin et al., "Stable photoluminescence of zinc oxide quantum dots in silica nanoparticles matrix prepared by the combined sol-gel and spray drying method", Journal of Applied Physics, 2001, vol. 89, No. 11, pp. 6431-6434.
Nakatsuka, "Surface Modification of Inorganic Pigments with Organic UV Absorbers", Colloids and Surfaces, 1988/89, vol. 34, pp. 323-334.
Hsu et al., "Paper Whiteners", Journal of Colloid and Interface Science, 1993, vol. 156, Issue 1, pp. 56-65.
Rottman et al., "Advanced Sunscreens: UV Absorbers Entrapped in Sol-Gel Glass Microcapsules", 2002, vol. 23, pp. 268-270.
Takeuchi et al., "Solid dispersion particles of tolbutamide prepared with fine silica particles by the spray-drying method", Powder Technology, 2004, vol. 141, pp. 187-195.
Tatapudy et al., "Benzyl Peroxide Microcapsules I. Preparation of Core Material", Indian Drugs, 1995, vol. 32, No. 6, pp. 239-248.
Hall et al., "Cocondensation of Organosilica Hybrid Shells on Nanoparticle Templates: A Direct Synthetic Route to Functionalized Core-Shell Colloids", Langmuir, 2000, vol. 16, No. 3, pp. 1454-1456.
Haq et al., "Preparation and properties of uniform coated inorganic colloidal particles 9. Titania on copper compounds", Colloids and Surfaces A: Physicochemical and Engineering Aspects, 1993, vol. 81, pp. 153-159.

(56) References Cited

OTHER PUBLICATIONS

Hench et al., "The Sol-Gel Process", Chemical Reviews, 1990, vol. 90, No. 1, pp. 33-72.
Iler, "Silica Gels", 1979, pp. 510-533.
Wenninger et al., "International Cosmetic Ingredient Dictionary and Handbook", 2000, vol. 2, pp. 1140-1147.
Kortesuo et al., "In vitro evaluation of sol-gel processed spray dried silica gel microspheres as carrier in controlled drug delivery", International Journal of Pharmaceutics, 2000, vol. 200, pp. 223-229.
Iskandar et al., "Control of the morphology of nanostructured particles prepared by the spray drying of a nanoparticle sol", Journal of Colloid and Interface Science, 2003, vol. 265, pp. 296-303.
Iskandar et al., "Preparation of microencapsulated powders by an aerosol spray method and their optical properties", Advanced Powder Technol., 2003, vol. 14, No. 3, pp. 349-367.
Jean et al., "$Y_2O_2S$:Eu Red Phosphor Powders Coated with Silica", Journal of the American Ceramic Society, 2000, vol. 83, No. 8, pp. 1928-1934.
Dun et al., "Layer-by-Layer Self-Assembly of Multilayer Zirconia Nanoparticles on Silica Spheres for HPLC Packings", Analytical Chemistry, 2004, vol. 76, No. 17, pp. 5016-5023.
Kortesuo et al., "Effect of synthesis parameters of the sol-gel-processed spray-dried silica gel microparticles on the release rate of dexmedetomidine", Biomaterials, 2002, vol. 23, pp. 2795-2801.
Yuan et al., "Organic Pigment Particles Coated with Colloidal Nano-Silica Particles via Layer-by-Layer Assembly", Chem. Mater., 2005, vol. 17, No. 14, pp. 3587-3594.
Kim et al., "Monodisperse hollow titania nanospheres prepared using a cationic colloidal template", Journal of Colloid and Interface Science, 2006, vol. 304, No. 2, pp. 370-377.
Van Bruggen, Preparation and Properties of Colloidal Core--Shell Rods with Adjustable Aspect Ratios, Langmuir, 1998, vol. 14, No. 9, pp. 2245-2255.
Rottman et al., "Advanced Sunscreens: UV Absorbers Entrapped in Glass Microcapsules", http://www.sol-gel.com, 2000, pp. 20-22.
Lapidot et al., "Advanced Sunscreens: UV Absorbers Encapsulated in Sol-Gel Glass Microcapsules", Journal of Sol-Gel Science and Technology, 2003, vol. 26, pp. 67-72.
Aizawa et al., "Preparation of Spherical Hydrous Silica Oxide Particles under Acidic Condition via Sol-Gel Processing", Journal of Sol-Gel Science and Technology, 2000, vol. 19, pp. 329-332.
Brinker et al., "The Physics and Chemistry of Sol-Gel Processing", Sol-Gel Science, 1990, pp. 562-563.
Bugnon, "Surface treatment of pigments. Treatment with inorganic materials", Progress in Organic Coatings, 1996, vol. 29 (1196), pp. 39-43.
Bugosh, "Colloidal Alumina—The Chemistry and Morphology of Colloidal Boehmite", Chemistry and Morphology of Colloidal Boehmite, 1961, vol. 65, pp. 1789-1793.
Butler et al., "An emulsion method for producing fine, low density, high surface area silica powder from alkoxides", Journal of Materials Science, 1996, vol. 31, pp. 1675-1680.
Chung et al., "Aqueous Synthesis of $Y_2O_2S$: Eu/Silica Core-Shell Particles", Journal of the American Ceramic Society, 2005, vol. 88, No. 5, pp. 1341-1344.
Matijević et al., "Coating of Nanosize Silver Particles with Silica", Journal of Colloid and Interface Science, 2000, vol. 221, Issue 1, pp. 133-136.
"Environmental Protection Agency", Federal Register, 2002, vol. 67, No. 94 and 40 CFR part 180, pp. 34616-34620.
Luis M. Liz-Marzan et al., "Synthesis of Nanosized Gold-Silica Core-Shell Particles," Langmuir, (1996), pp. 4329-4335, vol. 12.
T.P.M. Beelen, et al., "The Role of Aging on the Formation of Porous Silica," Preparation of Catalysts VI, (1995), pp. 33-48, Elsevier Science B.V.
"Ludox TM-50 colloidal silica," Sigma-Aldrich website: http://www.sigmaaaldrich.com/catalog/product/aldrich/420778?lang=en&region=US, downloaded Sep. 7, 2012.

Iler, Ralph K. Iler "The Chemistry of Silica, Solubility, Polymerization, Colloid and Surface Properties, and Biochemistry," John Wiley & Sons, (1979), pp. 366-367.
Zhu-Zhu Li et al., "Fabrication of Porous Hollow Silica Nanoparticles and Their Applications in Drug Release Control," Journal of Controlled Release, (2004) vol. 98, pp. 245-254.
U.S. Appl. No. 11/997,823, filed Sep. 9, 2008, by Toledano et al.
Stöber process; obtained from Wikipedia on Jul. 17, 2013; http://en.wikipedia.org/wiki/St%C3%B6ber_process.
Iler; *The Chemistry of Silica—Solubility, Polymerization, Colloid and Surface Properties, and Biochemistry*; 1979; pp. 366-367; John Wiley & Sons; U.S.A.
U.S. Appl. No. 12/525,329, filed Sep. 25, 2009 by Toledano et al.
U.S. Appl. No. 13/243,189, filed Sep. 23, 2011 by Lapidot et al.
U.S. Appl. No. 13/495,701, filed Jun. 13, 2012 by Toledano et al.
U.S. Appl. No. 90/011,440, filed Jan. 18, 2011 by Lapidot et al.
Bashir et al., *The Chemistry and Manufacture of Cosmetics*, vol. 1, 3$^{rd}$ edition, Chapter 5, pp. 163-182. (2000).
Breneman et al., "Double-blind, randomized, vehicle-controlled clinical trial of once-daily benzoyl peroxide/clindamycin topical gel in the treatment of patients with moderate to severe rosacea," *International Journal of Dermatology*, vol. 43, pp. 381-387, (2004).
Brinker et al., *Sol-Gel Science, The Physics and Chemistry of Sol-Gel Processing*, Academic Press, Inc., pp. 104-105, 134-135, 146-147, and 150-151, (1990).
Fireman et al., "A look at emerging delivery systems for topical drug products," *Dermatologic Therapy*, vol. 24, pp. 477-488, (2011).
Leyden et al., "Comparison of the Efficacy and Safety of a Combination Topical Gel Formulation of Benzoyl Peroxide and Clindamycin with Benzoyl Peroxide, Clindamycin and Vehicle Gel in the Treatments of Acne Vulgaris," *American Journal of Clinical Dermatology*, pp. 33-39, (2001).
Maibach, Howard, "Reduction of Skin Irritancy with Microsponge Topical Delivery," *Aesthetic Dermatology*, pp. 45-47, (2008).
Montes et al., "Topical Treatment of Acne Rosacea with Benzoyl Peroxide Acetone Gel," *Cutis*, vol. 32, pp. 185-190, (1983).
Nokhodchi et al., "The Effect of Formulation Type on the Release of Benzoyl Peroxide from Microsponges," *Iranian Journal of Pharmaceutical Sciences*, vol. 1, Issue 3, pp. 131-142, (2005).
Wester et al., "Controlled release of benzoyl peroxide from a porous microsphere polymeric system can reduce topical irritancy," *Journal of the American Academy of Dermatology*, vol. 24, No. 5, Part 1, pp. 720-726, (1991).
"Dimethyl Isosorbide," Lotioncrafter website: http://www.lotioncrafter.com (2013).
Yamasaki et al., "Increased serine protease activity and cathelicidin promotes skin inflammation in rosacea," *Nature Medicine*, vol. 13, No. 8, pp. 975-980, (2007).
M.P.B. van Bruggen., "Preparation and Properties of Colloidal Core—Shell Rods with Adjustable Aspect Ratios" Langmuir, 14(19):2245-2255.
Skapin et al "Preparation and coating of finely dispersed drugs 4. Loratadine and danazol" Journal of Colloid and Interface Science. 272:90-98 (2004).
Luo, Mingsheng and Tianhui Gao "The Extra Pharmaceutical Necessities", Sichuan Science and Technology Press, pp. 23-28, published on Mar. 31, 1993 (with English translation of relevant parts).
Goldgar et al. "Treatment options for acne rosacea. American family physician" Sep. 1, 2009;80(5):461-8.
Benzoyl Peroxide ("BPO", Chem and Tech. Assess. 2004, 61st JECFA, 1-6, http://www.fao.org/fileadmin/templates/ gns/pdf/jecfa/cla/63/Benzoylperoxide.pdf).
Culp et al. "Rosacea: a review" P & T: a peer-reviewed journal for formulary management. Jan. 2009;34(1):38.
Del Rosso et al. "Consensus recommendations from the American Acne & Rosacea Society on the management of rosacea, part 2: a status report on topical agents" Cutis. Dec. 2013;92(6):277-84.
Futamura et al. "A systematic review of Investigator Global Assessment (IGA) in atopic dermatitis (AD) trials: many options, no standards" Journal of the American Academy of Dermatology. Feb. 1, 2016;74(2):288-94.

(56) References Cited

OTHER PUBLICATIONS

Korting et al. "Current topical and systemic approaches to treatment of rosacea" Journal of the European Academy of Dermatology and Venereology. Aug. 1, 2009;23(8):876-82.
National Rosacea Society "All about Rosacea" downloaded Apr. 23, 2018 from: https://www.rosacea.org/patients/allaboutrosacea.php.
National Rosacea Society "New Study Examines Differences Between Rosacea and Acne" downloaded Apr. 23, 2018 from: https://www.rosacea.org/weblog/new-study-examines-differences-between-rosacea-and-acne.
National Rosacea Society 'Quick Links' downloaded Jun. 19, 2018 from: https://www.rosacea.org/.
Picardo et al. "Acne and rosacea" Dermatology and therapy. Jan. 1, 2017:7(1):S43-S52 (Suppl 1).
"Rosacea Causes & Treatment" downloaded Jun. 19, 2018 from: https://www.eruptingmind.com/rosacea-types-causes-treatments/.
Schueller and Romanowski, eds Conditioning agents for hair and skin. CRC Press, 1999. Table of Contents only (1999).
Van Zuuren et al. "Interventions for rosacea (Review)". Cochrane Database of Systematic Reviews, 2017, 476 pp.
Zhou et al. "Clinical characteristics and epidermal barrier function of papulopustular rosacea: A comparison study with acne vulgaris" Pakistan journal of medical sciences. 2016;32(6):1344.
Date, A. A., Naik, B., & Nagarsenker, M. S. (2006). Novel drug delivery systems: potential in improving topical delivery of antiacne agents. Skin Pharmacology and Physiology, 19(1), 2-16.

Büchel, G., Grün, M., Unger, K. K., Matsumoto, A., & Kazuo, T. (1998). Tailored syntheses of nanostructured silicas: control of particle morphology, particle size and pore size. Supramolecular Science, 5(3-4), 253-259.
Huo, Q., Feng, J., Schuth, F., & Stucky, G. D. (1997). Preparation of hard mesoporous silica spheres. Chemistry of Materials, 9(1), 14-17.
Nooney, R. I., Thirunavukkarasu, D., Chen, Y., Josephs, R., & Ostafin, A. E. (2002). Synthesis of nanoscale mesoporous silica spheres with controlled particle size. Chemistry of materials, 14(11), 4721-4728.
Nooney, R. I., Thirunavukkarasu, D., Chen, Y., Josephs, R., & Ostafin, A. E. (2003). Self-assembly of mesoporous nanoscale silica/gold composites. Langmuir, 19(18), 7628-7637.
Ozin, G. A. (1992). Nanochemistry: synthesis in diminishing dimensions. Advanced Materials, 4(10), 612-649.
"Cutis Benzoyl Peroxide Rosacea Study Summary" downloaded from (http://www.rosacea-treatment-clinic.com.au/Benzoyl-Peroxide/Benzoyl-Peroxide-Acetone.html) (2010).
Wenninger et al., "International Cosmetic Ingredient Dictionary and Handbook" Seventh Edition, vol. 2, pp. 1656-1662 (1997).
Tissot et al., "Hybrid Latex Particles Coated with Silica" Macromolecules, 34:5737-5739 (2001).
M.P.B. van Bruggen., "Preparation and Properties of Colloidal Core—Shell Rods with Adjustable Aspect Ratios" Langmuir, 14(19):2245-2255 (1998).

* cited by examiner

METHOD FOR PREPARING PARTICLES COMPRISING METAL OXIDE COATING AND PARTICLES WITH METAL OXIDE COATING

FIELD OF THE INVENTION

The present invention generally relates to method for preparation of particles comprising metal oxide coating layer and to compositions comprising particles with metal oxide coating.

BACKGROUND OF THE INVENTION

Metal oxides have been used as encapsulating materials and as matrices for various applications such as cosmetics, biomaterials, optics, laser, florescence, etc. using a variety of methods.

Shells consisting of hybrid inorganic-organic structures with bulk and surface properties that are compositionally controlled have been described in Hall, Simon, R., et al., Cocondensation of Organosilica Hybrid Shells on Nanoparticle, Templates: A Direct Synthetic Route to Functionalized Core—Shell Colloids, *Langmuir,* 16:1454-1456, 2000.

The formation of silica shells on core silver particles by a modified Stöber process is reported by Matijevi et al in *Journal of Colloid and Interface Science*, Volume 221, Issue 1, 1 Jan. 2000, Pages 133-136. They also report on the formation of spherical particles of Cu(II) basic carbonate coated with amorphous titania by hydrolysis of Ti(IV) butoxide in *Colloids and Surfaces A: Physicochemical and Engineering Aspects*, Volume 81, 13 Dec. 1993, Pages 153-159. In this report they show how the thickness of the shell could be varied by altering the experimental conditions. White pigments (whiteners) were prepared by coating monodispersed silica particles with titania. The hiding power of this powder was evaluated as a function of the particle diameter, the thickness of the titania shell, and the calcination temperature. Matijevi et al, *Journal of Colloid and Interface Science*, Volume 156, Issue 1, 1 Mar. 1993, Pages 56-65.

Colloidal boehmite (AlOOH) rods were used as cores for the preparation of rods with a silica shell as described in van Bruggen, M. P. B., Preparation and Properties of Colloidal Core—Shell Rods with Adjustable Aspect Ratios, *Langmuir,* 14:2245-2255, 1998.

A method for the encapsulation of fluorescent molecule into silica "nanobubbles" has been reported in Makarova, Olga V., et al., Adsorption and Encapsulation of Fluorescent Probes in Nanoparticles, *J. Phys. Chem. B,* 103:9080-9084, 1999. Bugnon, Philippe, (Bugnon, Philippe, Surface treatment of pigments. Treatment with inorganic materials, *Progress in Organic Coatings* 29: 39-43, 1996) has reported novel treatments of pigments with inorganic materials. Mikrajuddin, et al, (Mikrajuddin, et al., Stable photoluminescence of zinc oxide quantum dots in silica nanoparticles matrix prepared by the combined sol-gel and spray drying method, *Journal of Applied Physics,* 89:11, 2001) reported a ZnO/SiO2 nanocomposite with improved photoluminescence stability over ZnO colloids.

A spray drying approach has been used to apply 15-nm-thick $SiO_2$ continuous coatings onto ZnS:Ag phosphor particles as described in Villalobos, Guillermo, R., et al., Protective Silica Coatings on Zinc-Sulfide-Based Phosphor Particles, *J. Am. Ceram. Soc.,* 85(8):2128-2130, 2002.

Iskandar et al. have reported the preparation of microencapsulated powders by an aerosol spray method. The powders prepared by mixing two type of sols or sol-aqueous mixture precursor solution (Iskandar, Ferry, et al., Preparation of microencapsulated powders by an aerosol spray method and their optical properties, *Advanced Powder Technol.* 14(3):349-367, 2003). Iskandar et al. (Control of the morphology of nanostructured particles prepared by the spray drying of a nanoparticle sol. J Colloid Interface Sci., 265(2):296-303, 2003) additionally described the parameters influencing particles morphology by spray drying of silica nanoparticle sol.

Silica coating using layer by layer technique has been described in Dun, Huijuan, et al., Layer-by-Layer Self-Assembly of Multilayer Zirconia Nanoparticles on Silica Spheres for HPLC Packings, *Anal, Chem.,* 76:5016-5023, 2004; Yuan, Junjie, et al., Organic Pigment Particles Coated with Colloidal Nano-Silica Particles via Layer-by-Layer Assembly, *Chem. Mater.,* 17(4):3587-3594, 2005; Chung, Chau-Chyun, et al., Aqueous Synthesis of $Y_2O_2S$:Eu/Silica Core-Shell Particles, *J. Am. Ceram. Soc.,* 88(5):1341-1344, 2005.

Y2O2:Eu red phosphor Powders coated with silica using sol-gel and heterocoagulation techniques were described in Jean, Jau-Ho, et al., $Y_2O_2S$:Eu Red Phosphor Powders Coated with Silica, *J. Am. Ceram. Soc.,* 83(8):1928-1934, 2000.

Wilhelm, P., et al., (Wilhelm, P., et al, On-line tracking of the coating of nanoscaled silica with titania nanoparticles via zeta-potential measurements, Journal of Colloid and Interface Science, 293:88-92, 2006) reported nonoscaled spherical particles which were directly coated with titania nanoparticles by means of heterogenic coagulation.

The interaction between colloidal silica particles and the surface of ZnS-type phosphors has been studied in Merikhi, J., et al., Adhesion of Colloidal $SiO_2$ Particles on ZnS-Type Phosphor Surfaces, *Journal of Colloid and Interface Science,* 228:121-126, 2000.

Sodium Silicate utilized to obtain a $SiO_2$ coating on particles has been described in Wang, Hongzhi, et al., Effect of Polyelectrolyte Dispersants on the Preparation of Silica-Coated Zinc Oxide Particles in Aqueous Media, *J. Am. Ceram. Soc.,* 85(8):1937-1940, 2002; U.S. Pat. Nos. 2,885,366; 3,826,670.

The sources of silica gels and factors controlling gel characteristics were described in Iler Ralph K., The Chemistry of Silica, Wiley-Interscience publication, 1979, pp. 510-533. U.S. Pat. No. 6,303,290 describes the encapsulation of biomaterials in porous glass-like matrices prepared via an aqueous colloidal sol-gel process. This process includes entrapment of the biomaterial in silica cages forms by controlling the gel characteristics.

JP02-002867 and JP02-251240 disclose spherical particles made principally of silica, prepared by coprecipitation on of silica and UV filters such as benzophenone derivatives or dibenzoylmethane derivative, prepared in a water-in-oil emulsion.

U.S. Pat. No. 6,875,264 discloses a multilayer effect pigment including a transparent substrate, a layer of high refractive index material on the substrate, and alternating layers of low refractive index and high refractive index materials on the first layer. The high refractive index material may be titanium dioxide and the low refractive index material may be silicon dioxide.

U.S. Pat. No. 6,090,399 discloses a controlled release composition comprising one or more biologically active compounds incorporated into a metal oxide glass having a porous matrix.

U.S. Pat. Nos. 7,001,592 and 7,037,513 disclose a composition for topical application, e.g., a body-wash, where the additive contains a sol-gel encapsulated active either a sunscreen or a non-sunscreen. U.S. Pat. No. 7,052,913 discloses a biocompatible matrices, such as sol-gels encapsulating a reaction center, which may be administered to a subject for conversion of prodrugs into biologically active agents.

U.S. Pat. Nos. 6,303,149, 6,238,650, 6,468,509, 6,436,375, US2005037087, US2002064541, and International publication Nos. WO 00/09652, WO00/72806, WO 01/80823, WO 03/03497, WO 03/039510, WO00/71084, WO05/009604, and WO04/81222, disclose sol-gel microcapsules and methods for their preparation. EP 0 934 773 and U.S. Pat. No. 6,337,089 teach microcapsules containing core material and a capsule wall made of organopolysiloxane, and their production. EP 0 941 761 and U.S. Pat. No. 6,251,313 also teach the preparation of microcapsules having shell walls of organopolysiloxane. U.S. Pat. No. 4,931,362 describes a method of forming microcapsules or micromatrix bodies having an interior water-immiscible liquid phase containing an active, water-immiscible ingredient. Microcapsules prepared by a sol-gel process are also disclosed in GB2416524, U.S. Pat. No. 6,855,335, WO03/066209.

Another media, which can be utilized to protect sensitive ingredients, is doping within sol-gel matrices. In this method, monoliths, particles or other forms (such as thin films) are prepared, and the active ingredient is immobilized in the pores of the sol-gel matrix. The sol-gel matrix is doped with small amounts of the active ingredient. This method was utilized in WO98/31333, U.S. Pat. Nos. 6,495,352, and 5,292,801.

Thus there is a widely recognized need and will be highly advantageous to have a new process for metal oxide coating of a solid water insoluble particulate matter, enabling the growth of a metal oxide layer on said solid water insoluble particulate matter to the desired thickness and having the advantage of controlling and tuning of the thickness of the metal oxide layer. There is additionally a need for compositions especially for dermatological or agricultural use, characterized by the ability to isolate the active agent from the surrounding (by reducing its leaching through the metal oxide coating layer) thus lowering the side effects and toxicity associated with the active agent, and yet which are efficient at controlling the release of the active agent to the loci to be treated.

SUMMARY OF THE INVENTION

The present invention is based on the finding of a manner of obtaining a thick and dense coating of metal oxide on a solid water-insoluble particulate matter. The formation of the metal oxide layer by the new method is irreversible, i.e. it does not erode or disintegrate upon dispersion in water. The new method further enables to obtain a more dense layer and is capable of fine tuning of the width of the metal oxide layer, thus allowing better control of the release of the active ingredient from the microparticles upon application on a surface (such as skin or mucosal membrane, or pest-infested surface). The new method comprises treating the solid water-insoluble particulate matter with an ionic additive, e.g. a first cationic additive in an aqueous medium to obtain a dispersion of said particulate matter having positive charges on its surface; coating the particulate matter by precipitation of a metal oxide salt; and aging the coating layer. The coating is repeated at least 4 more times, preferably 4 to about 1000 more times, more preferably 4 to about 300 times, even more preferably 4 to about 100 times. The aging step is conducted at the end of the process. Most preferably aging is not conducted between repeated coating steps (i.e repeated coating steps of at least 4 more times), but only at the end of the process. The process includes additional steps as will be detailed below such as treating the so formed coating with a surface adhering second cationic additive to obtain positive charges on the coating, in order to modify the surface charge of the metal oxide layer to make it reactive for further coating by an additional metal oxide layer in a similar manner to that described above. Alternatively or in addition to said cationic additive, a non-ionic, surface adhering additive (e.g. a non-ionic polymer) may be used. Without being bound to theory such non-ionic additive may function as an adhesive material allowing precipitation of a further metal oxide layer on the coated metal oxide layer. The process may further include for example a step of separating the coated particulate matter such as by filtration, centrifugation or decantation; and optionally a step of washing and re-dispersing the obtained coated particulate matter in an aqueous medium.

The new method of preparation enables the formation and growth of a thick layer or layers of a metal oxide coating on the particulate matter, with the ability of fine control of the width of the obtained layer. This is particularly advantageous for certain uses where the active ingredient should be isolated, from its surroundings with an ability to be gradually released through the metal oxide layer. Exemplary uses are dermatological or cosmetic uses as well as in the case of pesticides for home, horticultural or agricultural use. The new method enables fine tuning and control of the thickness of the metal oxide layer.

Preferred is coating intended to achieve substantially the same or a larger therapeutic effect of the active agent and reduced side effects compared to an uncoated composition of the active agent.

According to one aspect of the present invention there is provided a process for coating a solid, water-insoluble particulate matter, with a metal oxide comprising:

(a) contacting the solid, water-insoluble particulate matter with an ionic additive and an aqueous medium to obtain a dispersion of said particulate matter having positive charges on its surface;
(b) subjecting the particulate matter to a coating procedure comprising precipitating a metal oxide salt onto the surface of the particulate matter to form a metal oxide layer thereon to thereby obtain particulate matter coated by a metal oxide coating layer;
(c) repeating step (b) at least 4 more times; and
(d) aging said coating layer.

According to another aspect of the present invention there is provided coated particulate matter obtained by the process as described in the present invention.

According to yet another aspect of the present invention there is provided a method for treating a surface condition in a subject, comprising topically administering onto the surface a composition comprising coated particulate matter as described in the present invention, the particulate matter being a topically dermatologically active agent.

According to additional aspect of the present invention there is provided use of coated particulate matter as described in the present invention, the particulate matter being a topically dermatologically active agent, for topical administration on the skin or mucosal membrane.

According to a further aspect of the present invention there is provided a method for preventing, reducing, or eliminating pests at a locus, comprising applying to the locus of said pest a pesticidaly effective amount of a pesticidal composition comprising a coated particulate matter as described in the present invention, the particulate matter being a pesticide.

Also provided by the invention are particles comprising a particulate matter coated by a metal oxide layer wherein: (i) said metal oxide layer has a width of 0.1-10 micron; and (ii) said particles are characterized in that when tested in a Dissolution Tester using Paddle Method in a medium, typically an organic-based solvent such as acetonitrile, isopropyl miristate, ethanol or methanol, in which said particulate matter is soluble, and a dissolution volume in which the concentration of the particulate matter is lower than the solubility of the particulate matter, the time for releasing 50% w/w of the particulate matter from said particles is at least two-fold higher, preferably three-fold higher, more preferably five-fold higher and most preferably ten-fold higher as compared to the dissolution of the free form of the particulate matter having substantially the same particle size diameter as the particulate matter in said particles.

Further provided by the invention are particles comprising a core composed of a solid, water insoluble particulate matter; said core is coated by a metal oxide layer; wherein said metal oxide layer is substantially not in an amorphous and/or not in a crystalline form. The term "said metal oxide layer is substantially not in an amorphous and/or not in a crystalline form" is meant to denote that distinct regions of amorphous metal oxide (in case the metal oxide in its pure form is amorphous) or crystalline metal oxide (in case the metal oxide in its pure form contains crystalline material, or is purely crystalline) cannot be detected by methods such as X-Ray diffraction. The non-amorphous and/or non-crystalline metal oxide layer refers to a co-structured composite of metal oxide and an adhering additive. Such adhering additive may be for example a polymer which interrupts the formation of continues regions of the metal oxide, thereby leading to the non-amorphous and non crystalline metal oxide form. The non amorphous and non crystalline metal oxide form is characterized by not having any X-ray diffraction peak specific to the metal oxide in its pure form. For example if the metal oxide in its pure form is amorphous, a characteristic X-ray diffraction peak or peaks may be detected. This may be the case, for example, in case of a particle with a pure metal oxide coating. In the case of the particles according to this aspect of the invention, the characteristic X-ray diffraction peak(s), specific to the amorphous form is absent, shifted, or flattened. An example are particles with a silica-based coating, which will have a different peak—namely absent, shifted, or flattened—as compared to particles with an amorphous silica coating. In the case of a metal oxide which in its pure form contains crystalline regions, or is purely crystalline, in the case of a composite coating a peak specific to the crystalline form is absent, shifted, or flattened. Thus, X-ray diffraction may serve to distinguish particles of this aspect of the invention over others.

BRIEF DESCRIPTION TO DRAWINGS

FIG. 1 shows the release rate of BPO for sample SGT025, prepared according the coating procedure in Example 1, using step 2b: coating option #2. Number of repeating coating was 20, 30, 40. Aging was conducted for 96 hours at 25 C. The release rate is compared to free BPO.

Figure 2:
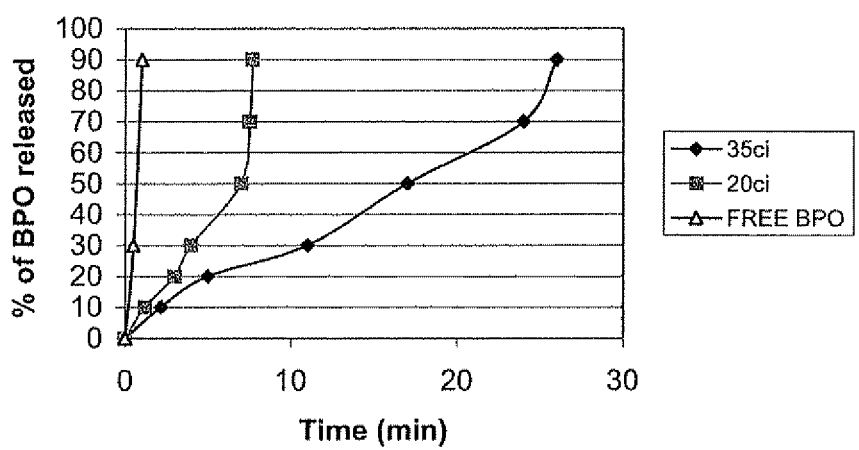

FIG. 2 shows the release rate of BPO for sample SGT010, prepared according the coating procedure in Example 1, using step 2a: coating option #1. Number of repeating coating was 20, 35. Aging was conducted for 72 hours at 25 C. The release rate is compared to free BPO.

DETAILED DESCRIPTION OF THE INVENTION

The present invention relates to a process for coating a solid, water-insoluble particulate matter, with a metal oxide comprising:
(a) contacting the solid, water-insoluble particulate matter with an ionic additive and an aqueous medium to obtain a dispersion of said particulate matter having positive charges on its surface;
(b) subjecting the particulate matter to a coating procedure comprising precipitating a metal oxide salt onto the surface of the particulate matter to form a metal oxide layer thereon thereby to obtain particulate matter coated by a metal oxide coating layer;
(c) repeating step (b) at least 4 more times; and
(d) aging said coating layer.

As used herein the term "solid, water-insoluble particulate matter" refers to a solid material having solubility in water of less than 1% w/w, typically less than 0.5% and at times less than 0.1% w/w at room temperature (20° C.).

The "solid, water-insoluble particulate matter" constitutes the "core" of the particles obtained by the process. The solid, water-insoluble particulate matter, is preferably in such a state of subdivision that it can be suspended in water, e.g. in the form of a finely-divided powder having a $D_{90}$ (see definition below), preferably in the range of 0.3-50 micron. Such a particulate matter can readily be suspended in an aqueous systems by stirring, with or without the aid of a surfactant. The "solid, water-insoluble particulate matter" may be comprised of the active ingredient per se or may be comprised of the active ingredient and excipients (e.g. solid carrier).

The terms "solid, water-insoluble particulate matter" and "particulate matter" will be used interchangeably.

In the present invention the terms "layer", "coating" and similar terms, refer to a layer of metal oxide formed around a particle or particulate matter. The layer or coating may not always be complete or uniform and may not necessarily lead to complete coverage of the particulate matter or particle surface. It is appreciated that upon repetition of the coating steps as the coating process proceeds a more uniform coating and more complete coverage of the particulate matter is obtained.

The term "dispersion" as used herein in step (a) of the process refers to a solid dispersion of the particulate matter in the aqueous medium.

Step (a) of the process may further comprise reducing the particle size of the particulate matter to the desired particle size for example by milling or homogenization.

The core (i.e. solid, water insoluble particulate matter) may be of any shape for example rod-like, plate-like, ellipsoidal, cubic, or spherical shape.

Referring to size of particles will be through their $D_{90}$ meaning that 90% of the particles have the stated dimension or less (measured by volume). Thus, for examples, for spherical particles stated to have a diameter of 10 micrometer ("microns"), this means that the particles have a $D_{90}$ of 10 microns. The $D_{90}$ may be measured by laser diffraction. For particles having a shape other than spheres, the $D_{90}$ refers to the mean average of the diameter of a plurality of particles.

In the case of cores having a spherical shape, the diameter ($D_{90}$) may be in the range of 0.3 to 90 microns, preferably 0.3 to 50 microns, more preferably 1 to 50, even more preferably 5 to 30 microns.

By the term "$D_{90}$ may be in the range of 0.3 to 90 microns" is meant that 90% by volume of the particles (in this case the particle's core) may be less than or equal to a value in the range of 0.3 to 90 microns.

For generally cubic-shaped cores or cores having a shape resembling that of a cube, the mean size of a side may be in the range 0.3 to 80 microns, preferably 0.3 to 40 microns, more preferably 0.8 to 40, even more preferably 4 to 15 microns.

For rod-like shaped, ellipsoidal-shaped and plate-like shaped cores, the largest dimension (that of the longest axis) is typically in the range 10 to 100 microns, preferably 15 to 50 microns; and the smallest dimension is typically in the range 0.5 to 20 microns, and more preferably 2 to 11 microns.

As used herein, unless otherwise indicated, the term "particle" refers to the metal oxide coated particulate matter.

It is appreciated that some of the particles obtained by the process may at times be formed from two or more original particles of the solid, water-insoluble particulate matter and may accordingly include at times more than one core, such cores being separated from each other by a metal oxide region.

The core may be an organic or inorganic material. Preferably the core is composed of a material other than a metal oxide.

The weight of the solid, water-insoluble particulate matter (core material) based on the total weight of the particle may be in the range 99%-50% w/w, more preferably in the range 97%-50% w/w. The core material may be in a crystalline form, amorphous form, or combination thereof. The core material may be a cosmetically, pharmaceutically or an agrochemical active ingredient.

Preferably step (c) of the process described above is repeated 4 to about 1000 times. This means that preferably step (b) of the process described above is repeated 4 to about 1000 times.

Preferably the process comprising repeating step (c) 4 to about 300 times, and more preferably 4 to about 100 times. Even more preferably step (c) of the process described above is repeated 5-80 times and most preferably 5-50 times. This means that preferably step (b) is repeated as indicated above with respect to step (c).

By the term "repeated 4 to about 1000 times" is meant that the process may be repeated 4, 5, 6, 7, 8, 9 . . . , etc. times up to and including about 1000 times.

According to a preferred embodiment of the present invention step (d) further comprising after aging, separating the coated particulate matter from the dispersing aqueous medium, such as by filtration, centrifugation or decantation and optionally rinsing and redispersing the obtained coated particulate matter in an aqueous medium.

During the coating process it is preferred that at least 50% of the content the particulate matter (active agent) in the aqueous medium is in a solid state during the coating process.

According to a preferred embodiment of the present invention the process comprising:
(a) contacting the solid, water-insoluble particulate matter, with a first cationic additive and an aqueous medium to obtain a dispersion of said particulate matter having positive charges on its surface;
(b) subjecting the particulate matter to a coating procedure comprising precipitating a metal oxide salt onto the surface of the particulate matter to form a metal oxide coating layer on the particulate matter;
(b1) in an aqueous medium, contacting the coated particulate matter with a surface adhering additive being one or both of (i) a second cationic additive, and (ii) a non-ionic additive;
(b2) subjecting the particulate matter obtained in step (b1) to a coating procedure as in step (b);
(c) repeating steps (b1) and (b2) at least 3 more times; and
(d) aging the metal oxide coating layer.

Preferably the process comprising repeating step (c) 3 to about 1000 times.

Preferably the process comprising repeating step (c) 3 to about 300 times, and more preferably 3 to about 100 times.

As used herein by the term "repeating step (c) 3 to about 1000 times" is meant that the process may be repeated 3, 4, 5, 6, 7, 8, 9, . . . etc. times up to and including about 1000 times.

This means that preferably steps (b1) and (b2) are repeated as indicted above with respect to step (c).

Additionally according to a preferred embodiment of the present invention the process comprising:
(a) contacting the solid, water-insoluble particulate matter, with an anionic additive, a first cationic additive and an aqueous medium to obtain a dispersion of said particulate matter having positive charges on its surface;
(b) subjecting the particulate matter to a coating procedure comprising precipitating a metal oxide salt onto the surface of the particulate matter to form a metal oxide coating layer on the particulate matter;
(b1) in an aqueous medium, contacting the coated particulate matter with a surface adhering additive being one or both of (i) a second cationic additive and (ii) a non-ionic additive;
(b2) subjecting the particulate matter obtained in step (b1) to a coating procedure as in step (b);
(c) repeating steps (b1) and (b2) at least 3 more times; and
(d) aging the metal oxide coating layer.

When an anionic additive and first cationic additive are used in step (a) of the process, preferably the anionic additive is added before the first cationic additive.

Step (c) may be repeated 3 to about 1000 times. Preferably step (c) is repeated 3 to about 300 times, and more preferably 3 to about 100 times. This means that preferably steps (b1) and (b2) are repeated as indicted above with respect to step (c).

The ionic additive (such as first cationic additive) used in step (a) of the process have a dual effect: to form positive charges on the surface of the particulate matter as will be described below, and also to serve as a wetting agent, thus allowing dispersion of the particulate matter as discrete core particles, where each core particle is individually suspended in the aqueous medium.

Step (a) of the process may be conducted for example by (i) contacting the particulate matter with dry ionic additives and then suspending both in an aqueous medium to obtain a dispersion of said particulate matter having positive charges on its surface, or alternatively by (ii) suspending the solid, water-insoluble particulate matter in an aqueous medium comprising ionic additives to obtain a dispersion of said particulate matter having positive charges on its surface.

According to another preferred embodiment of the process may comprise (a) contacting the solid, water-insoluble particulate matter, with an ionic additive selected from (i) an anionic additive; (ii) a first cationic additive, and a combination thereof, and an aqueous medium to obtain a dispersion of said particulate matter having positive charges on its surface; (b), (b1), (b2), (c), (d) are as described herein.

The concentration of the ionic additives in the dispersion can be about 0.001% to about 30%, preferably about 0.01% to about 10% w/w and most preferably about 0.1% up to about 5% w/w. The solid content of the water dispersion can be about 0.1% to about 80% w/w, preferably about 1% to about 60% w/w most preferably about 3% to about 50% w/w.

The purpose of step (a) is to modify the electrical charge of the particulate matter by using ionic additives such that it will be made reactive to the attachment of the metal oxide layer.

For preparing the core material of the particles, the particulate matter ought to be suitably coated with an ionic additive (e.g. cationic additive), such that it can be attached to the precipitated metal oxide salt.

Preferably the ionic additive is selected from a cationic additive, an anionic additive, and a combination thereof. The cationic additive may be a cationic surfactant and/or cationic polymer. The anionic additive may be an anionic surfactant and/or anionic polymer.

The particulate matter is contacted with an ionic additive, for example by mixing it with a solution of a cationic surfactant and/or cationic polymer or an anionic surfactant and a cationic additive (e.g. cationic surfactant and/or cationic polymer). Cationic and anionic surfactants are particularly effective in being adsorbed upon the surface of the particulate matter. The ionic additive may also be anionic polymers used in combination with a cationic additive. The cationic surfactant and/or the cationic polymer and optionally further the anionic surfactant (or anionic polymer) need to be used in sufficient amount to provide positive charges on the surface of the particulate matter. A monolayer of the ionic additive is preferred, but the coating need not be continues. It is sufficient that there are at least spots of cationic additive. These spots will then serve as anchors for the attachment of the metal oxide layer. It is preferred that there are fairly uniform distribution of these anchoring points on the core surface so that as the metal oxide layer builds up it will bridge over and be firmly attached to the core.

According to one preferred embodiment said first and said second cationic additive are the same.

According to another preferred embodiment said first and said second cationic additive are different.

More preferably the first ionic additive is a an anionic surfactant and the second ionic additive is a cationic polymer Most preferably the first cationic additive is a cationic surfactant and the second cationic additive is a cationic polymer.

According to another preferred embodiment, the first cationic additive is a cationic surfactant and the additive in step (b1) is a non-ionic additive (e.g. a non-ionic polymer).

Preferably the coated particulate matter and the second cationic additive are mixed, and most preferable said mixing is under vigorous stirring (e.g. mixer speed above 1000 rpm).

According to a preferred embodiment of the present invention the process further comprising following step (d): (e) separating the coated particulate matter from the aqueous medium and optionally rinsing and redispersing the coated particulate matter in an aqueous medium.

Preferably the separation of the coated particulate matter is conducted by a method such as filtration, centrifugation, decantation, dialysis, or by evaporation of the aqueous medium.

Additionally according to a preferred embodiment of the present invention, step (b) comprises adding a metal oxide salt to the aqueous medium; and optionally acidifying the aqueous medium.

Further according to a preferred embodiment of the present invention, step (b2) comprises adding a metal oxide salt to the aqueous medium; and optionally acidifying the aqueous medium.

Preferably step (b1) further comprising adjusting the pH of the dispersion obtained in (b) to a value higher than the isoelectric point of the metal oxide before adding the second cationic additive, more preferably to a pH value of at least about 1 unit higher than the isoelectric point of the metal oxide, before adding the second cationic additive.

Preferably step (b1) further comprising adjusting the pH of the dispersion obtained in (b) to a value higher than the isoelectric point of the metal oxide before adding one or both of (i) a second cationic additive, and (ii) a non-ionic additive, more preferably to a pH value of at least about 1 unit higher than the isoelectric point of the metal oxide, before adding one or both of (i) a second cationic additive, and (ii) a non-ionic additive.

For example, in case the metal oxide is silica (e.g. having an isoelectric point in the range 1.7-2.5) the preferred pH may be at least in the range of about 2.5-6.5.

The purpose of the pH adjustment of the dispersion to a value higher than the isoelectric point of the metal oxide is to form negatively charged metal oxide on the particulate matter surface that will be bound to the positive charges of the second cationic additive thus enabling the attachment of the second cationic additive to the surface of the particulate matter.

The non-ionic additive is of a kind that adheres to the surface ("surface-adherent"). An example is a non-ionic polymer. The non-ionic additive may be used alone or in addition to the second cationic surfactant. Without wishing to be bound by theory, the surface-adherent property may be through hydrogen-binding groups such as hydroxyl or amine groups. This allows adhesion of a further layer of metal oxide on the preceding precipitated metal oxide layer.

Preferably the particulate matter/metal oxide salt weight ratio, in each of the steps (b) or (b2) is about 5,000/1 to about 20/1, preferably about 5,000/1 to about 30/1, or about 5,000/1 to about 40/1, more preferably about 1,000/1 to about 40/1, and most preferably about 500/1 to about 80/1.

Preferably the particulate matter/cationic additive ratio, in step (b1) is about 25,000/1 to about 50/1, preferably about 5,000/1 to about 100/1, and most preferably about 2000/1 to about 200/1.

According to preferred embodiment the particulate matter/metal oxide salt weight ratio, in each of the steps (b) or (b2) is about 5,000/1 to about 65/1, and more preferably about 1000/1 to about 100/1.

Preferably the particulate matter/cationic additive weight ratio, in step (b1) is about 10,000/1 to about 100/1, and more preferably about 5000/1 to about 200/1.

The aging in step (d) is crucial for obtaining a strengthened and dense layer of metal oxide.

Preferably step (d) comprises raising the pH to a value in the range 3-9 and mixing the suspension in this pH.

According to a preferred embodiment of the present invention step (d) comprises raising the pH to a value in the range 3-9 and mixing the suspension in this pH for a period of at least 2 h.

According to a preferred embodiment of the present invention step (d) comprises raising the pH to a value in the range 3-9, preferably to a range of 5-7, and mixing, e.g. by stirring, the suspension (dispersion) in this pH range e.g. for a period of at least 2 h (two hours). Preferably stirring is for 2-96 h, more specifically 2-72 h, more preferably at least 10 h (for example 10-72 h). The stirring is preferably a gentle stirring, preferably in the range 200-500 rpm.

Upon completion of aging, the separation (e.g. filtration, centrifigation or decantation) will be easy to perform (due to the hard metal oxide layer formed) and the obtained cake or concentrated dispersion will be easily re-dispersed in an aqueous medium to form a dispersion of particles.

The purpose of aging in step (d) is to obtain a strengthened and denser layer of metal oxide.

In the absence of the aging step a thinner and softer layer of metal oxide would be obtained since the metal oxide salt upon precipitation forms a gel layer of metal oxide which may disintegrate or erode upon separation and washing or by mechanical stirring.

The aging may be conducted at a temp of 4-90° C., preferably at 15-60° C. and most preferably the aging is conducted at a temperature 20° C.-40° C.

Thus the repeated steps of coating and aging at the end of the process also enable the growth of thicker and stronger layer of metal oxide. Most preferably aging is not conducted between the repeated coating steps (i.e. between the repeated coating step (b)), but only at the end of the process. Thus most preferably the aging is conducted only at the end of the process described herein.

According to certain embodiments, the process may further comprise adding a colloidal metal oxide suspension, preferably aqueous-based suspension (comprising nanometric metal oxide (nanoparticles of metal oxide)) during the coating procedure. Preferably the colloidal metal oxide suspension is selected from colloidal silica suspension, colloidal titania suspension, colloidal alumina suspension, colloidal zirconia suspension, colloidal ZnO suspension, and mixtures thereof. The colloidal metal oxide suspension may be added during the coating process (e.g. in step (b) in one or more of its repeated steps). Preferably the size of the nanometric metal oxide in diameter is in the range between 5-100 nm (average particle size diameter). The weight ratio of the nanometric metal oxide to the metal oxide salt may be in the range 95:5 to 1:99 preferably 80:20 to 5:95 more preferably 70:30 to 10:90, most preferably about 60:40 to 20:80. The weight ratio of the nanometric metal oxide to the metal oxide salt may be about 50:50.

According to other embodiments, the process does not include addition of colloidal metal oxide suspension during the coating process. According to this embodiment nanometric metal oxide particles (nanoparticles of metal oxide) are not added during the coating process.

As used herein, the term "metal oxide coating layer" or "metal oxide layer" encompasses the product of both a single processing step as well as a product of the process in which the initially coated particles are further processed, by the repeated processing steps of step (c), described above.

The solid, water insoluble particulate matter may be a pharmaceutically, cosmetically, or agrochemical active ingredient.

Preferably the solid, water insoluble particulate matter is a dermatological active agent.

Preferably the dermatological active agent is selected from antifungal agents, antibacterial agents, anti-inflammatory agents, antipuritic agents, anti psoriatic agent, and anti acne agents. The dermatological agent may also be combinations of any of the above agents.

The antibacterial agents may be a bacteriostatic or bacteriocidal drug.

The dermatological active agent may be for example antifungal agents such as ketoconazole, bacteriostatic drugs such as metronidazole or erythromycin, bactericidal drugs such as bacitracin, corticosteroids such as mometasone furoate, methylprednisolone aceponate, prednicarbate, triamcinolone acetonide, fluocinonide, desoximetasone, bethasone valerate or mometasone furoate, antipruritic agent such as doxepin hydrochloride, and anti acne agents such as benzoyl peroxide, azelaic acid, retinoids such as tretinoin (all trans retinoic acid), tazarotene, iso-tretinoin or adapalene.

More preferably the active agent (e.g. anti-acne agent) is selected from benzoyl peroxide, retinoid, and mixtures thereof.

Most preferably the active agent (e.g. anti-acne agent) is benzoyl peroxide.

The agrochemical agent may be a pesticide.

Pesticides which may be employed in the practice of this invention include a wide range of herbicides, nematocides, insecticides, acaricides, fungicides, plant growth promoting or controlling chemicals and other crop treating products which are solids at ambient temperatures. One of ordinary skill in the art can find a listing of suitable pesticides by consulting references such as the Ashgate Handbook of Pesticides and Agricultural Chemicals, G. W. A. Milne (ed.), Wiley Publishers (2000). Combinations of two or more pesticides may also be employed.

Illustrative examples of the pesticides which may be employed are Azoxystrobin, Carbendazim, Chlorothalonil, Copper-oxychloride, Cyazofamid, Cymoxanil Cymoxanil, Cyproconazole, Dimethomorph, Epoxiconazole, Fluazinam, Flusilazole, Flutolanil, Folutriafol, Kresoxim-methyl, Mancozeb, Maneb, Pencycuron, Pyraclostrobin, Tebuconazole, Thiophanate-methyl, Trifloxystrobin, Ziram, Aclonifen, Ametryn, Amicarbazone, Atrazine, Bentazone, Chlorimuron-ethyl, Cyhalofop-butyl, Ethalfluralin, Ethofumasate, Florasulam, Flufenacet, Flumetsulam, Fomesafen, Halosulfuron-methyl, Imazamox, Imazapic, Imazethapyr, Imazapyr, Imazaquin, Isoproturon, Isoxaflutole, Lactofen, Linuron, Mesotrione, Metamitron, Metazachlor, Metoxuron, Metribuzin, Metsulfuron-methyl, Oxyfluorfen, Pendimethalin, Prometryn, Propanil, Quinclorac, Quinmerac, Quizalofop-ethyl, Quizalofop-P-ethyl, Rimsulfuron, Simazine, Sulcotrione, Sulfentrazone, Sulfometuron-methyl, Sulfosulfuron, Tebuthiuron, Thifensulfuron-methyl, Tralkoxydim, Triasulfuron, Triclopyr, Trifluralin, Abamectin, Acetamiprid, Aldicarb, Alphacypermethrin, Betacyfluthrin, Bifenthrin, Carbofuran, Chlorfenapyr, Chlorfluazuron, Chlorpyrifos, Cypermethrin, Deltamethrin, Endosulfan, Esfenvalerate, Fipronil, Imidacloprid, Indoxacarb, Lambdacyhalothrin, Lufenuron, Methoxyfenozide, Novaluron, Oxamyl, Pirimicarb, Spinosad, Teflubenzuron, Thiacloprid, Thiamethoxam, Fenamiphos, Thidiazuron, Sulphur, and mixtures of any of the above.

Preferably the metal oxide is selected from Silica, Titania, Alumina, Zirconia, ZnO, and mixtures thereof. Most preferably the metal oxide is silica.

The metal oxide salt is preferably an alkali metal oxide salt, e.g. a sodium or potassium salt.

According to a preferred embodiment of the present invention the metal oxide salt is selected from sodium silicate, potassium silicate, sodium aluminate, potassium aluminate, sodium titanate, potassium titanate, sodium zirconate, potassium zirconate, and mixtures thereof. Most preferably the metal oxide salt is a silicate salt.

Further according to a preferred embodiment of the present invention the ionic additive is selected from a cationic surfactant, anionic surfactant, a cationic polymer, and mixtures thereof. When an anionic surfactant is used, preferably a cationic additive is further added such as a cationic surfactant and/or a cationic polymer.

Preferably the cationic additive is selected from a cationic surfactant, a cationic polymer, and mixtures thereof.

According to a preferred embodiment the first cationic additive is a cationic surfactant, and the second cationic additive is a cationic polymer.

The first cationic additive is preferably a cationic surfactant.

Preferably the cationic surfactant is selected from monoalkylquaternary ammonium salts, dialkyl quaternary ammonium salts, and mixtures thereof.

Preferably the monoalkylquaternary ammonium salts are selected from benzethonium chloride, benzalkonium chloride, cetyltrimethylammonium chloride (CTAC), cetyltrimethylammonium bromide (CTAB), lauryltrimethylammonium chloride, stearyltrimethylammonium chloride, cetylpyridinium chloride, and mixtures thereof.

Most preferably the monoalkylquaternary ammonium salt is cetyltrimethylammonium chloride.

Preferably the dialkyl quaternary ammonium salt is distearyldimethylammonium chloride.

Additional cationic surfactants which can be used are described in: John A. Wenninger et al. (Editors) *International Cosmetic Ingredient Dictionary and Handbook* (Eighth Edition 2000), Vol. 2 pp. 1140-1147, Published by The cosmetic, Toiletry, and Fragrance Association, incorporated herein by reference in its entirety.

The ionic additive may be an anionic surfactant.

Preferably the anionic surfactant is selected from alkyl benzene sulphonic acids and salts, alkyl ether carboxylic acids and salts, alkyl sulphosuccinamates, alkyl sulphossucinates, alpha olefin sulphonates, aromatic hydrocarbon sulphonic acids and salts, fatty alcohol ethoxy sulphates, fatty alcohol sulphates, phosphate esters, and mixtures thereof.

Preferably the alkyl benzene sulphonic acid salt is sodium dodecyl benzene sulphonate, the fatty alcohol sulphate is sodium lauryl sulphate, the alkyl sulphossucinates is sodium dioctyl sulphossucinate, and mixtures thereof. The anionic surfactant may be mixtures of any of the above.

Additional anionic surfactants which can be used are described in: John A. Wenninger et al. (Editors) *International Cosmetic Ingredient Dictionary and Handbook* (Eighth Edition 2000), Vol. 2 pp. 1140-1147, Published by The cosmetic, Toiletry, and Fragrance Association, incorporated herein by reference in its entirety.

Preferably the weight ratio of the ionic additive to the water-insoluble particulate matter is in the range 1:1000-1:10, more preferably in the range 1:200-1:50, most preferably about 1:100. The ratios indicated above refer to an ionic additive such as the first cationic additive or to the combination of a first cationic additive and an anionic additive. The second cationic additive may be a cationic polymer, a cationic surfactant, or mixtures thereof. The cationic surfactant may be as described above.

According to a preferred embodiment of the present invention the second cationic additive is a cationic polymer.

Preferably the weight ratio of the first coated particulate matter (i.e. in step (b1)) to the second cationic additive is in the range of about 25,000/1 to about 50/1, more preferably about 5,000/1 to about 100/1 most preferably about 2000/1 to about 200/1.

Preferably the weight ratio of the further processed coated particulate matter (e.g. in the repeated steps described in step (c)) to the second cationic additive is in the range of about 25,000/1 to about 50/1, more preferably about 5,000/1 to about 100/1 most preferably about 2000/1 to about 200/1.

Preferably the particulate matter/cationic additive weight ratio, in step (b1) is about 10,000/1 to about 100/1, and more preferably about 5000/1 to about 200/1.

Preferably the weight ratio of the further processed coated particulate matter (e.g. in the repeated steps described in step (c)) to the second cationic additive is in the range of about 10,000/1 to about 100/1, and more preferably about 5000/1 to about 200/1.

In case a non-ionic additive (e.g. non-ionic polymer) is used alone or in addition to the second cationic additive, the weight ratios of the of the first coated particulate matter to the (i) non-ionic additive or (ii) a combination of a non-ionic additive and second cationic additive, and the weight ratios of the further processed coated particulate matter to the (i) non-ionic additive or (ii) the combination of the non-ionic additive and second cationic additive, may be as indicated above with respect to the second cationic additive.

Preferably the cationic polymer (of the first cationic additive or second cationic additive) is selected from poly (ethyleneimine) (PEI), poly(dimethyldiallylammonium chloride) (PDAC), poly(acrylamide-co-diallyl-dimethylammonium chloride) (polyquaternium-7), poly(allylamine hydrochloride) (PAH), Chitosan, polylysine, and mixtures thereof.

The second cationic polymer may also be a copolymer of non-ionic and ionic monomers such as pyrrolidone/dimethylaminoethyl methacylate copolymer.

According to another preferred embodiment of the present invention the second cationic additive is selected from colloidal alumina, colloidal ceria (CeO2), colloidal alumina coated silica (such as Ludox CL, Sigma-Aldrich), and mixtures thereof.

The second cationic additive may be a colloidal metal oxide bearing a positive charge such as described above (e.g. colloidal alumina, colloidal ceria (CeO2), colloidal alumina coated silica, or mixtures thereof).

The non-ionic additive used in the process is preferably a non-ionic polymer. The non-ionic polymer may be for example polyvinylalcohol, polyvinylpyrrolidone, and mixtures thereof.

Further according to a preferred embodiment of the present invention, the process further comprises drying the obtained coated particulate matter.

Still further according to a preferred embodiment of the present invention, the drying is by a method selected from spray drying, lyophilization, oven drying, vacuum drying, and fluidized bed.

Additionally, according to a preferred embodiment of the present invention, the process further comprises chemically modifying the surface of the coated particulate matter.

The surface chemical modification preferably comprises modifying the metal oxide surface with organic groups, preferably hydrophobic groups.

Preferably process comprising attaching hydrophobic groups to the surface of the metal oxide layer.

The purpose of attaching hydrophobic groups to the surface of the metal oxide layer is to control the water penetration rate into the particles and consequently to control the release of the active agent from the particles. Modifying the surface of the metal oxide layer by hydrophobic groups enables to further control the release of the active agent from the particles, according to the desired rate.

The hydrophobic groups may be for example an alkyl silane, dialkyl silane, trialkyl silane, (such alkyl groups may be further substituted with one or more fluoro atoms), aryl silane (such as benzyl silane, or phenyl silane), diaryl silane, or triaryl silane.

Moreover according to a preferred embodiment of the present invention, the chemical surface modification comprises reacting silanol groups on the surface of the metal oxide layer with precursors selected from monohalotrialkyl silane such as chlorotrimethylsilane, dihalodialkyl silane such as dichlorodimethyl silane, trihaloalkyl silane such as trichloromethylsilane, monoalkoxytrialkyl silane such as methoxy tri methyl silane, dialkoxydialkyl silane such as dimethoxydimethylsilane, trialkoxyalkyl silane such as trimethoxymethylsilane, aryltrihalosilane such as phenyltrichlorosilane, diaryldihalosilane such as diphenyldichlorosilane, triarylhalosilane such as triphenylchlorosilane, aryltrialkoxysilane such as phenyltrimethoxysilane, diaryldialkoxysilane such as diphenyldimethoxysilane, triarylalkoxysilane such as triphenylmethoxysilane, and mixtures thereof.

Preferably the alkyl group includes 1-18 carbon atoms, more preferably 1-6 carbon atoms. Most preferably the alkyl is methyl. The alkyl groups may be substituted by one or more fluoro atoms. Preferably the alkoxy group includes 1-6 carbon atoms and more preferably 1-2 carbon atoms.

The halo group may be for example chloro, bromo, iodo, fluoro. Most preferably the halo groups are chloro and bromo.

The aryl is preferably phenyl or benzyl.

The precursors react with the silanol groups on the surface of the metal oxide layer to form a siloxane bond.

The attachment of the hydrophobic groups to the surface of the metal oxide layer can be performed by reacting the dried coated particulate matter with the above precursors. The procedure for attaching hydrophobic groups to the metal oxide can be conducted as follows: a dried powder of coated particulate matter is suspended in an organic solvent such as toluene. A precursor (hydrophobization reagent) from the list above such as dimethyldichlorosilane is added to the organic phase (mixture), optionally in the presence of a halogen scavenger such as trialkyl amine or triethanol amine. The organic mixture is refluxed for at least about 24 hours to obtain coverage of the metal oxide layer with the hydrophobic groups via attachment of the hydrophobic groups to the silanol groups on the surface of the metal oxide layer.

Further according to a preferred embodiment of the present invention the obtained metal oxide coating layer has a width (thickness) of about 0.1, 0.2, 0.3, 0.5, 0.7, 1, 1.5, 2 or 5 micron or above, preferably up to 10 micron.

The width of the metal oxide layer may be determined for example by a Transmission Electron Microscope or Confocal Microscope such that in a circular cross sectional area of the particle the smallest width is at least e.g. 0.1 micron (the width is determined as the smallest distance from the surface of the particle (i.e. metal oxide surface) to the core-metal oxide interface).

The invention additionally relates to the coated particulate matter obtained by the processes as described in the present invention.

According to a preferred embodiment of the present invention, the weight ratio of the metal oxide to the solid, water-insoluble particulate matter, is in the range of 1:99 to 40:60. The weight ratio may also be in the range 1:99 to 50:50. Preferably the weight ratio of the metal oxide to the solid, water-insoluble particulate matter, is in the range of 10:90 to about 20:80. The weight ratio may also be as described in the present invention.

According to a preferred embodiment of the present invention the particles (coated particulate matter) have a diameter of 0.5-100 micron. More preferably the diameter of the particles is in the range 1-50 micron and most preferably in the range 2-30 micron.

The particles may be useful for cosmetic or medical applications.

The particles may also be used in agricultural or polymeric industry.

The particles may be useful for any application wherein the active ingredient should be isolated, temporally or permanently from the ambient surroundings.

It is appreciated that the particles of the present invention are composed of distinct regions of the metal oxide layer and the core material (i.e. the solid water insoluble particulate matter). The core material in newly prepared particles is preferably substantially free of the metal oxide and further the metal oxide layer is preferably substantially free of said core material, e.g. either as particle dispersion (in the nanometric range of below 0.1 micron) of the water insoluble particulate matter or as molecular dispersion of said water insoluble particulate matter. Thus, according to a preferred embodiment of the present invention the metal oxide layer in newly prepared particles, is substantially free of core material (either as molecules or as nanometric particles). The term "substantially free" in this context denotes that the concentration of the molecules of the core material or the concentration of the nanometric particles of the core material is negligible as compared to the metal oxide. Similarly, by the term "the core material is substantially free of the metal oxide" is meant that the concentration of the metal oxide in the core, is negligible as compared to the core material.

The invention further relates to a pharmaceutical, cosmetic or cosmeceutical composition for topical administration comprising a carrier; and a plurality of coated particulate matter obtained by the process described in the present invention, each of said particles comprising a solid, water insoluble dermatologically active agent, coated by a metal oxide layer.

The carrier may be a cosmetic or pharmaceutically acceptable carrier. The coated dermatologically active agent is preferably dispersed in the carrier.

The coated dermatological active agent may be easily dispersed or suspended in a carrier or diluent.

Simple mixing with any suitable mixer or carrier is sufficient to achieve an effective dispersion. If necessary, high shear forces may be applied to facilitate fast and efficient mixing of the coated particles in the carrier.

The particles are preferably non-leaching when dispersed in a carrier, and most preferably non-leaching in an aqueous-based carrier.

By the term "non-leaching" it is meant that the leaching of the particulate matter (active agent) from the particles into an aqueous-based liquid is less than 5% w/w, preferably less than 1% w/w and most preferably less than 0.5% w/w at room temperature (20° C.), under gentle agitation for 1 hour or until a steady state concentration is achieved. Typically, said aqueous-based liquid is water. The values indicated above refer to the percentage of the active agent leached into an aqueous medium relative to the initial amount of the active agent in the particles. The leaching values indicated above refer preferably to a dispersion having a concentration of the particulate matter in the aqueous medium higher than 0.1% w/w, more preferably higher than 1% w/w, and most preferably higher than 10% w/w.

The metal oxide coating of the present invention is highly advantageous since it is capable of isolating the solid, water insoluble particulate matter from its surrounding medium, and yet enables the release the particulate matter upon application to the surface to be treated.

Preferably the dermatological active agent is selected from antifungal agents, antibacterial agents, anti-inflammatory agents, antipuritic agents, anti psoriatic agent, anti acne agents, and mixtures thereof.

Preferably the anti-acne agent is selected from benzoyl peroxide, a retinoid, and mixtures thereof.

Preferably the retinoid is all trans retinoic acid (ATRA), iso-tretinoin, tazarotene or adapalene.

Most preferably the anti-acne agents are benzoyl peroxide (BPO) and all trans retinoic acid (ATRA).

BPO and ATRA are particularly preferred compounds for coating with a metal oxide in accordance with the invention. The purpose of the BPO and ATRA coating is to provide at least one of the following benefits: a) to reduce the skin irritation of the BPO and ATRA crystals, b) to significantly reduce side effects caused by BPO and ATRA in topical formulations, c) to increase the dispersability of BPO and ATRA crystals in aqueous solutions in the absence of surfactant, d) to prevent direct contact of the BPO and ATRA crystals from the skin, e) prevent additional crystal growth processes of BPO and ATRA after grinding, f) to increase the stability of the BPO and ATRA, g) to have good compatibility with other ingredients in the formulation, h) to produce a sustained release mechanism of BPO and ATRA onto the skin.

According to a preferred embodiment of the present invention, the metal oxide is selected from Silica, Titania, Alumina, Zirconia, ZnO, and mixtures thereof. Most preferably the metal oxide is silica.

Further according to a preferred embodiment of the present invention, the weight ratio of said metal oxide to said solid, water-insoluble particulate matter, is in the range 1:99 to 40:60. The weight ratio may be in the range 3:97 to 50:50. The weight ratio of the metal oxide layer to the solid, water-insoluble particulate matter, may be also in the range 5:95 to 40:60, 10:90 to 40:60, 5:95 to 30:70, or 10:90 to 30:70.

Still further according to a preferred embodiment of the present invention, the weight ratio of said metal oxide to said solid, water-insoluble particulate matter, is in the range 10:90 to 20:80.

Moreover according to a preferred embodiment of the present invention, the particles (coated particulate matter) have a diameter of 0.5-100 micron.

The thickness of said metal oxide layer may be as described above.

Additionally according to a preferred embodiment of the present invention, the thickness of said metal oxide layer is in the range 0.1-10 micron.

Further according to another preferred embodiment of the present invention, the thickness of said metal oxide layer is in the range 0.3-10 micron.

The carrier may be in the form of ointment, a cream, a lotion, an oil, an emulsion, a gel, a paste, a milk, an aerosol, a powder, a foam, a wash. Most preferably the carrier is in the form of a gel or a cream more preferably oil-in-water cream. Most preferably the dispersing phase (i.e. the carrier) is aqueous based and comprises water as dispersing medium.

Additionally according to a preferred embodiment of the present invention, the composition is for the treatment of a disease or condition selected from acne, infection, inflammation, puritis, psoriasis, seborrhea, contact dermatitis, rosacea, and a combination thereof.

Further according to a preferred embodiment of the present invention, the dermatological agent is selected from antifungal agents, antibacterial agents, anti-inflammatory agents, antipuritic agents, anti psoriatic agent, and anti acne agents.

The antifungal agents, antibacterial agents, anti-inflammatory agents, antipuritic agents, anti psoriatic agent, and anti acne agents may be as described in the present invention above.

Most preferably the dermatological active agent is an anti-acne agent.

Moreover according to a preferred embodiment of the present invention, the anti acne agent is selected from benzoyl peroxide, retinoid, and mixture thereof.

Most preferably the anti-acne agent is selected from benzoyl peroxide, tretinoin (ATRA), and mixtures thereof.

According to a preferred embodiment of the present invention the metal oxide is selected from Silica, Titania, Alumina, Zirconia, ZnO, and mixtures thereof.

Additionally according to a preferred embodiment of the present invention, the weight ratio of said metal oxide to said solid, water-insoluble dermatological active agent, is in the range 1:99 to 40:60. The weight ratio of the metal oxide layer to the solid, water-insoluble particulate matter, may be also in the range 1:99 to 40:60, 5:95 to 40:60, 5:95 to 30:70, or 10:90 to 30:70.

Further according to a preferred embodiment of the present invention, the weight ratio of said metal oxide to the solid, water-insoluble particulate matter, is in the range 10:90 to 20:80. The weight ratios may also be as detailed above with respect to the weight ratio of the metal oxide to the solid, water-insoluble particulate matter.

Moreover according to a preferred embodiment of the present invention, the particles have a diameter of 0.5-100 micron. Preferably the particles have a diameter of 0.8-100 micron, more preferably 1-50 micron and most preferably 5-30 micron.

Additionally according to a preferred embodiment of the present invention, the thickness of said metal oxide layer is in the range 0.1-10 micron. The thickness may be as defined above in relation to the process. Typical thickness is about 0.1-3 micron, preferably about 0.1-1 micron. The thickness of the metal oxide layer may also be in the range about 0.3 to 3 micron, and most preferably about 0.3 to 2 micron.

According to a preferred embodiment of the present invention, the carrier is in the form of an ointment, a cream, a lotion, an oil, an emulsion, a gel, a paste, a milk, an aerosol, a powder, a foam, or a wash.

The invention further relates to a method for treating a surface condition in a subject, comprising topically administering onto the surface a composition comprising a coated particulate matter as described in the present invention, the particulate matter being a topically dermatologically active agent.

According to a preferred embodiment the coated particulate matter is obtained by the process of the present invention.

It is appreciated that the compositions of the present invention may comprise a plurality of coated particulate matter.

Preferably the subject is a mammal, and most preferably the mammal is a human.

The term "treating" or "treatment" as used herein includes any treatment of a condition (disease or disorder) associated with a patient's body surface such as the skin or mucosal membrane, and includes inhibiting the disease or disorder (i.e. arresting its development), relieving the disease or disorder (i.e. causing regression of the disease or disorder), or relieving the conditions caused by the disease (i.e. symptoms of the disease). The concentrations of the dermatological agents that can be used for treatment of a specific disease or disorder may be as described in The Merck index an encyclopedia of chemical, drugs, and biologicals/The Merck index an encyclopedia of chemical, drugs, and biologicals. Rahway, NJ; Merck & Co; 1989., incorporated herein by reference in its entirety.

Although individual needs may vary, determination of optimal ranges for effective amounts of the compositions is within the skill of the art. Generally, the dosage required to provide an effective amount of a pharmaceutical composition, which can be adjusted by one skilled in the art, will vary depending on the age, health, physical condition, weight, type and extent of the disease or disorder of the recipient, frequency of treatment, the nature of concurrent therapy (if any) and the nature and scope of the desired effect(s).

According to a preferred embodiment of the present invention, the surface of a subject body is skin or mucosal membrane.

The surface condition may be a disease or disorder selected from acne, infection, inflammation, puritis, psoriasis, seborrhea, contact dermatitis, rosacea, and a combination thereof.

According to a preferred embodiment of the present invention, the metal oxide layer releases the particulate matter following topical application (administration). Preferably the solid, water insoluble particulate matter is a dermatological active agent as described above in the present invention, more preferably an anti-acne agent, and most preferably the dermatological active agent (e.g. anti acne agent) is benzoyl peroxide.

According to another preferred embodiment the dermatological active agent (e.g. anti acne agent) is a retinoid (preferably tretinoin).

Without being bound to theory it is assumed that benzoyl peroxide is released from the particles through the metal oxide coating layer by extraction by lipids available on the skin. Upon application on the skin, it is assumed that the skin lipids diffuse through the metal oxide layer and extract the benzoyl peroxide present in the core. Other dermatological agents may be similarly released from the particles.

The invention further relates to the use of coated particulate matter as described in the present invention, the particulate matter being a topically dermatologically active agent, for the preparation of a medicament for topical administration on the skin or mucosal membrane.

The topical administration is preferably for treating a disease or disorder selected from acne, psoriasis, seborrhea, rosacea contact dermatitis, infection, inflammation, puritis, and any combination thereof.

According to a preferred embodiment of the present invention, the surface of the metal oxide later of the coated particulate matter may be chemically modified by organic groups, preferably hydrophobic groups, attached to its surface.

The hydrophobic groups may be for example an alkyl groups (such alkyl groups may be further substituted with one or more fluoro atoms), aryl groups (such as benzyl or phenyl), and combinations thereof. The groups may be as described above with respect to the process.

Also provided by the invention are particles comprising a particulate matter coated by a metal oxide layer wherein: (i) said metal oxide layer has a width of 0.1-10 micron; and (ii) said particles are characterized in that when tested in a Dissolution Tester using Paddle Method in a medium, typically an organic-based solvent such as acetonitrile, isopropyl miristate, ethanol or methanol, in which said particulate matter is soluble, and a dissolution volume in which the concentration of the particulate matter is lower than the solubility of the particulate matter, the time for releasing 50% w/w of the particulate matter from said particles is at least two-fold higher, preferably at least three-fold higher, preferably at least four-fold higher, more preferably at least five-fold higher and most preferably at least ten-fold higher as compared to the dissolution of the free form of the particulate matter having substantially the same particle size diameter as the particulate matter in said particles.

The dissolution of the free form of the particulate matter is measured under the same conditions as the coated particulate matter. The time for releasing 50% w/w of the particulate matter (active agent) from the particles is compared to the time of 50% w/w dissolution of the free form. Preferably the dissolution volume is such that the concentration of the particulate matter is lower than at least half of the solubility of the particulate matter. The "solubility" relates to the solubility of the particulate matter (active ingredient) in the dissolution medium (e.g. an organic-based solvent such as acetonitrile, isopropyl miristate, ethanol or methanol). It is appreciated that the dissolution volume will also depend on the detection level of the analytical method. The dissolution may be conducted at a temperature of 20 C-40 C. The dissolution may be conducted at a paddle rate of 50-200 rpm.

Pesticide Compositions and Uses

In one aspect, the present invention is directed to pesticidal compositions comprising the coated pesticides described above. Typically, such compositions are comprised of the coated pesticide and an agriculturally acceptable carrier. Such carriers are well know in the art and may be solids or liquids.

Other Components

To the extent that the compositions contain other components, these components make up minor portions of the composition. Minor components may also include free pesticide, which has not been incorporated into the coated pesticide. In addition to the other components listed herein, compositions of this invention may also contain carriers, such as water or other solvents in amounts for example equal to or greater than the major components.

The coated pesticides of this invention may be formulated and/or applied with one or more second compounds. Such combinations may provide certain advantages, such as, without limitation, exhibiting synergistic effects for greater control of pests, reducing rates of application of pesticide thereby minimizing any impact to the environment and to worker safety, controlling a broader spectrum of pests, resistance of crop plants to phytotoxicity, and improving tolerance by non-pest species, such as mammals and fish.

Second compounds include, without limitation, other pesticides, fertilizers, soil conditioners, or other agricultural chemicals. The compositions of the present invention may also contain additional surface active compounds as dispersants. Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. Surface-active agents, when used, normally comprise 1 to 20% weight of the composition.

One skilled in the art will, of course, recognize that the formulation and mode of application of a pesticide may affect the activity of the material in a given application. Thus, for agricultural use, the present coated pesticides may be formulated as a granular of relatively large particle size (for example, 8/16 or 4/8 US Mesh) (e.g. agglomerates of coated particulate matter of the pesticide that may redisperse in water to the primary coated particulate matter), as water-dispersible granules, as powdery dusts, as wettable powders, as suspension concentrates, as capsule suspension (coated particulate matter, in suspension), or as any other known types of agriculturally-useful formulations, depending on the desired mode of application. They may be applied in the dry state (e.g., as granules, powders, or tablets) or they may be formulated as concentrates (e.g., solid, liquid, gel) that may be diluted to form stable dispersions (suspensions).

Concentrates

The compositions may be formulated as concentrates by techniques known to one of ordinary skill in the art. If the composition is to be formulated as a solid, a filler such as Attaclay may be added to improve the rigidity of the granule.

The coated pesticides and pesticidal formulations may be stored and handled as solids which are dispersible into stable aqueous emulsions or dispersions prior to application. The dispersions allow uniform application from water. This is particularly advantageous at the field point of use, where normal admixing in water is all that is required before application.

The compositions of the present invention may also be in the form of wettable powders. Wettable powders are finely divided particles that disperse readily in water or other dispersant. The wettable powder is ultimately applied to the locus where pest control is needed either as a dry dust or as a dispersion in water or other liquid. Typical carriers for wettable powders include Fuller's earth, kaolin clays, silicas, and other highly absorbent, readily wet inorganic diluents. Wettable powders normally are prepared to contain about 5-80% of pesticide, depending on the absorbency of the carrier, and usually also contain a small amount of a wetting, dispersing or emulsifying agent to facilitate dispersion. For example, a useful wettable powder formulation contains 80.0 parts of the pesticidal compound, 17.9 parts of clay and 1.0 part of sodium lignosulfonate and 0.3 part of sulfonated aliphatic polyester as wetting agents. Additional wetting agent and/or oil will frequently be added to a tank mix to facilitate dispersion on the foliage of the plant.

Water-Dispersible Granules (WDG or DG) are dry compositions of the coated pesticide that will disperse in water yielding a dispersion of primary particles. Pesticide contents may range from 10-70% w/w. Polymers are used as dispersants (polyacrylate salts and lignosulfonate salts) and as binders to hold the granule together. Advantages of the dry product are that less potential for hydrolysis exists and high pesticide content may be achievable. Disadvantages are a more complex process involving milling blending extrusion and drying. Usually excipients are solids in this formulation.

Other useful formulations for the pesticidal compositions of the invention include suspo-emulsions, flowable formulations, and suspension concentrates.

Flowable formulations consist of particles of the pesticide complex (coated particulate matter of the pesticide) suspended in a liquid carrier, generally water. Flowables, may include a small amount of a surfactant as a wetting agent and dispersants that are generally anionic or nonionic, and will typically contain pesticides in the range of 5% to 95%, frequently from 10 to 50%, by weight of the composition. For application, flowables may be diluted in water or other liquid vehicle, and are normally applied as a spray to the area to be treated.

Suspension concentrates (SC) are dispersions of finely divided (2-15 micron) water-insoluble solid particles of the pesticide complex in water. Pesticide contents range from 8-50% w/w. They are pourable, easily dispersible in water and should be stable to settling in the package. Polymers such as xanthan gum are used to prevent settling by increasing the yield stress of the suspension. Some polymeric dispersants, such as polyacrylic acid salts, are used. The dispersions may be stabilized against flocculation by use of polymers such as methacrylate grafted with polyethylene glycol (Atlox). Ethylene oxide/propylene oxide copolymers may be used to provide some stabilization after dilution.

Suspo-emulsions (SE) are dispersions of water immiscible liquids and finely divided (2-15 micron) water-insoluble solid particles of the pesticide complex (coated particulate matter of the pesticide) in water. Pesticide contents range from 8-50% w/w. They are pourable, easily dispersible in water and should be stable to settling in the package. They contain several surfactants, in order to both stabilize the particles and emulsify the liquids. Some polymeric dispersants, such as polyacrylic acid salts, are used. SEs, like SCs, may be stabilized against flocculation by use of polymers such as methacrylate grafted with polyethylene glycol (Atlox). Ethylene oxide/propylene oxide copolymers may be used to provide some stabilization after dilution.

Useful formulations include suspensions of the coated pesticide in a relatively non-volatile solvent such as water, corn oil, kerosene, propylene glycol, or other suitable solvents. Granular formulations, wherein the coated pesticide is carried on relative coarse particles, are of particular utility for aerial distribution or for penetration of cover crop canopy. Pressurized sprays, typically aerosols wherein the coated pesticide is dispersed in finely divided form as a result of vaporization of a low-boiling dispersant solvent carrier may also be used. Water-dispersible granules are free flowing, non-dusty, and readily water dispersible. In use by the farmer on the field, the granular formulations, suspo-emulsions, flowable concentrates, etc., may be diluted with water to give a concentration of pesticide in the range of e.g., 0.2-2%.

Method of Controlling Pests

In a further aspect, this invention is directed to a method of controlling pests comprising applying to the locus of such pests a pesticidally effective amount of the pesticidal compositions described herein. Such locus may be where pests are present or are likely to become present.

Thus the invention additionally relates to a method for preventing, reducing, or eliminating pests at a locus, comprising applying to the locus of said pest a pesticidaly effective amount of a pesticidal composition comprising a coated particulate matter as described in the present invention the particulate matter being a pesticide.

According to preferred embodiment of the present invention the method is for preventing pest infestation at a locus, comprising introducing said coated particulate matter onto a surface or into a substrate prone to pest attack.

The locus may be any location where pests are found or are expected to be found for example foliage, soil or porous surfaces such as cement, wood, ceramics and similar surfaces.

The pesticide may be as described in the present invention. Preferably the pesticide is selected from carbofuran, imidacloprid, thiamethoxam, tebuconazole, indoxacarb and pyrethroids including bifenthrin, cypermethrin, alphacypermethrin, deltamethrin, and lambda-cyhalothrin.

In applying the compositions of this invention, whether formulated alone or with other agricultural chemicals, an effective amount and concentration of the active compound is of course employed; the amount may vary in the range of, e.g. about 0.001 to about 3 kg/ha, preferably about 0.03 to about 2 kg/ha. For field use, where there are losses of pesticide, higher application rates (e.g., four times the rates mentioned above) may be employed.

The pesticidal compositions of this invention may be applied either as water-diluted sprays, or dusts, or granules to the areas in which suppression of pests is desired. These formulations may contain as little as 0.1% to as much as 35% or more by weight of pesticide. Dusts are free flowing admixtures of the pesticide compositions of the invention with finely divided solids such as talc, natural clays, kieselguhr, flours such as walnut shell and cottonseed flours, and other organic and inorganic solids which act as dispersants and carriers for the pesticide. These finely divided solids have an average particle size of less than about 50 microns. A typical dust formulation useful herein is one containing 1.0 part or less of the pesticidal composition and 99.0 parts of talc.

Different application methods are used for the pesticide formulations depending on the target pest, e.g., weed, fungus, or insect, and on the type of crop being treated. Application of pesticide may be by spraying solutions, emulsions or dispersions of finely divided pesticide complex to achieve accurate and even concentration over the entire treated area or target. Usually, the water used to dilute the pesticide composition in the spray mixture amounts to approximately 5-80 gallons per acre and the active ingredient amount may range approximately from 20 to 1000 grams per acre.

Pesticides may also be applied by broadcast spreading of granular formulations using machinery to achieve even distribution over the entire target. The coated pesticide may be incorporated into granular formulations by using a sticker (additional surfactant, polymer solution, or latex) to attach the pesticide to an inert support. Other granules are prepared by extrusion of powdered pesticide complex with inert powdered ingredients, water, binders, and dispersants to form granules that are subsequently dried. Pre-formed granular supports are often used to absorb liquid pesticide or solutions of the pesticide.

It is appreciated that the coated particulate matter, coating metal oxide layer, particulate matter, etc. described in the invention in a particular aspect may be characterized by the various features, properties, etc. as described in the present invention in the other aspects.

EXAMPLES

In the examples below, all % values referring to a solution are in (w/w). All % values, referring to dispersions are in (w/w).

All solutions used in the examples below unless otherwise stated refer to an aqueous solution of the indicated ingredient.

Example #1

Silica Coating of BPO

Step 1: milling: 110 g. of hydrous BPO 75% (USP grade from Sigma) were suspended in 152 g. of 0.4% CTAC solution containing 0.001% silicon antifoam. The BPO was milled using a stator rotor mixer (Kinematika polytron 6100 operated at 15,000 rpm/25 m/s). The milling was stopped when the particle size distribution (PSD) of the suspension was d(0.9)<35 µm or the temperature has reached 50 C. The final suspension was cooled to room temperature.

Step 2a: coating option #1: During the coating procedure the suspension was stirred with a mechanical dissolver, 80 mm, at 500 RPM at all times. The pH of the milled BPO suspension was corrected to 8 using NaOH 5N solution. A portion of 1 g of 15% sodium silicate solution (15% w/w as $SiO_2$) was added and the suspension was stirred for 5 min. A portion of 1 g of 3% Polyquaternium 7 was added and the suspension was stirred for 5 min. pH was adjusted to 6-7 using 5N HCl solution.

This procedure was repeated for 5-100 times in order to create a series of silica layers around BPO having different thickness.

Step 2b: coating option #2: During the coating procedure the suspension was stirred with a mechanical dissolver, 80 mm, at 500 RPM at all times. The pH of the milled BPO suspension was corrected to 8 using NaOH 5N solution. A portion of 2.5 g of 15% sodium silicate solution (15% w/w as $SiO_2$) was added and the suspension was stirred for 5 min. A portion of 2.5 g of 3% Polyquaternium 7 was added and the suspension was stirred for 5 min. pH was adjusted to 6-7 using 5N HCl solution.

This procedure was repeated for 5-100 times in order to create a series of silica layers around BPO having different thickness.

The aging step: The coated BPO suspension at pH 6.5 was kept for aging at room temperature (25 C+/−2) under gentle agitation for 24 hrs.

Example #2

Analytical Evaluation of the BPO Release:

The release profile of BPO out of the silica shell was done in a water/Acetonitrile solution, which is capable of dissolving BPO. The method is based on the strong oxidation properties of BPO. BPO reacts with potassium iodine (KI) ions to form $I_2$, which gives a color reaction. $I_2$ is than reduces back to $I^-$ using sodium thiosulfate (STS) to eliminate the color. Each 12.11 mg of oxidizing BPO was reduced by 1 ml of 0.1M STS.

Solution A is composed of deionized water, acetone, 0.1M STS solution and KI.

The following table includes the ratios between the components in order to distinguish a certain % of released BPO.

| % released BPO | % acetone | % 0.1M STS soln. | % KI | % dionized water |
|---|---|---|---|---|
| 10 | 60 | 3.67 | 4.5 | 31.83 |
| 20 | 60 | 7.34 | 4.5 | 28.16 |
| 30 | 60 | 11.01 | 4.5 | 24.49 |
| 50 | 60 | 18.35 | 4.5 | 17.15 |
| 70 | 60 | 25.69 | 4.5 | 9.81 |
| 90 | 60 | 33.03 | 4.5 | 2.47 |

Suspension B, preparation of BPO: weigh 200 mg of BPO as 100% (1 g as 20% suspension) into 5 ml measuring bottle and fill with deionized water up to 5 ml.

Procedure: Into 50 ml glass beaker add 40 ml of solution A and the 5 ml of suspension B and measure the time for yellow color appearance.

The following table summarizes the results obtained for encapsulated (coated) BPO as described in example #1.

| Sample | CS | # oEC | ATm | ATp | *10 | *20 | *30 | *50 | *70 | *90 |
|---|---|---|---|---|---|---|---|---|---|---|
| Free BPO | — | 0 | 0 | — | | | 0.5 | | | 1 |
| SGT010 | 2a | 20 | 72 | 25 | 1.2 | 3 | 4 | 7 | 7.5 | 7.66 |
| SGT010 | 2a | 35 | 72 | 25 | 2.2 | 5 | 11 | 17 | 24 | 26 |
| SGT025 | 2b | 20 | 96 | 25 | 3 | 7 | 10.3 | 19.3 | 28 | 29.5 |
| SGT025 | 2b | 30 | 96 | 25 | 4.6 | 12.3 | 23 | 40 | 60 | 68 |
| SGT025 | 2b | 40 | 96 | 25 | 7 | 25 | 32 | 69 | 113 | 123 |
| SGT025 | 2b | 40 | 96 | 40 | 7 | 21 | 47 | 80 | 140 | 170 | oEC—number of repeating coating as described in example #1
CS—coating step as described in example #1
ATm—aging time in hours
ATp—aging temperature in Celsius.
*(10, 20 . . . ) - time (in min.) for (10, 20 . . . ) % of BPO released from the capsule (coated BPO).

The release rates of BPO of Samples SGT 025 and SGT 010 are shown in FIGS. 1 and 2.

Discussion:

It is clearly shown that the higher the amount of silica added per encapsulation (coating) cycle and/or the higher the number of coating cycles, the longer the time for BPO release.

Example #3

Silica Coating of Tretinoin (ATRA)

Step 1: milling: 75 g. of all trans Retinoic acid (ATRA) (USP grade from Rhodia) are suspended in 250 g. of 0.3% CTAC solution containing 0.001% silicon antifoam. The ATRA is milled using a M-110Y microfluidizer processor (Microfluidics) at 15,000 psi. The milling is stopped when the particle size distribution (PSD) of the suspension is $d(0.9)<20$ μm. The temperature is kept below 30 C at all times.

Step 2: coating: During the coating procedure the suspension is stirred with a mechanical dissolver, 80 mm, at 500 RPM at all times. The pH of the milled ATRA suspension is corrected to about 4 using HCl 5N solution. A portion of 0.5 g of 15% sodium silicate solution (15% w/w as $SiO_2$) is added and the suspension is stirred for 5 min. A portion of 0.5 g of 3% Polyquaternium 7 is added and the suspension is stirred for 5 min. pH is readjusted to about 4 using 5N HCl solution.

This procedure is repeated for 5-100 times in order to create a series of silica layers around ATRA having different thicknesses.

The aging step: The coated ATRA suspension at pH 4.5 is kept for aging at room temperature under gentle agitation for 24 hrs.

Example #4

Silica Coating Using Anionic Surfactant

Step 1: milling: 110 g. of hydrous BPO 75% (USP grade from Sigma) were suspended in 152 g. of 0.4% sodium dodecyl sulphonate (SDS) solution containing 0.005% silicon antifoam. The BPO was milled using a stator rotor mixer (Kinematika polytron 6100 operated at 15,000 rpm/25 m/s). The milling was stopped when the particle size distribution (PSD) of the suspension was $d(0.9)<35$ μm or the temperature has reached 50 C. The final suspension was cooled to room temperature and a portion of 1-2.5 g of 3% Polyquaternium 7 was added and the suspension was stirred for 5 min.

Step 2a: coating option #1: During the coating procedure the suspension was stirred with a mechanical dissolver, 80 mm, at 500 RPM at all times. The pH of the milled BPO suspension was corrected to 8 using NaOH 5N solution. A portion of 1 g of 15% sodium silicate solution (15% w/w as $SiO_2$) was added and the suspension was stirred for 5 min. A portion of 1 g of 3% Polyquaternium 7 was added and the suspension was stirred for 5 min. pH was adjusted to 6-7 using 5N HCl solution.

This procedure was repeated for 5-100 times in order to create a series of silica layers around BPO having different thickness.

Step 2b: coating option #2: During the coating procedure the suspension was stirred with a mechanical dissolver, 80 mm, at 500 RPM at all times. The pH of the milled BPO suspension was corrected to 8 using NaOH 5N solution. A portion of 2.5 g of 15% sodium silicate solution (15% w/w as $SiO_2$) was added and the suspension was stirred for 5 min. A portion of 2.5 g of 3% Polyquaternium 7 was added and the suspension was stirred for 5 min. pH was adjusted to 6-7 using 5N HCl solution.

This procedure was repeated for 5-100 times in order to create a series of silica layers around BPO having different thickness.

The aging step: The coated BPO suspension at pH 6.5 was kept for aging at room temperature (25 C+/−2) under gentle agitation for 24 hrs.

Example #5

Silica Coating of Tretinoin (ATRA), Using Non-Ionic Polymer

Step 1: milling: 12.5 g. of tretinoin were suspended in 250 g. of 0.3% CTAC solution containing 7.5 g BHT. The tretinoin was milled using a M-110Y microfluidizer processor (Microfluidics) at 5,000 psi. The milling was stopped when the particle size distribution (PSD) of the suspension was $d(0.9)<13$ μm. The temperature has kept below 30 C at all times.

Step 2: coating: During the coating procedure the suspension was stirred with a mechanical stirrer at all times. The pH of the milled ATRA suspension was about 3.5. A portion of 1 g of 15% sodium silicate solution (15% w/w as $SiO_2$) was added and the suspension was stirred for 5 min. HCl 1 M was added until the pH of the solution was about 3. A portion of 1 g of 1% polyvinyl alcohol water solution was added and the suspension was stirred for 5 min.

This procedure was repeated 50 times in order to create silica layers around ATRA.

The aging step: The coated tretinoin suspension was kept for aging at room temperature at pH 3 under gentle agitation for 24 hrs.

Example #6

Silica Coating of Bifenthrin Using Cationic Polymer 3.58 grams of cetyltrimethylammonium chloride (CTAC) (29% w/w aqueous solution) were added to 196.5 grams of deionized water in a 1 liter flask. 50.5 grams of dry milled bifenthrin technical (having an average particle size of about 15 microns) were added, and the mixture was homogenized using a Polytron PT 6100 Homoginizer. 216 grams of the resulting dispersion were transferred to a Mettler Toledo LabMax Automatic Lab Reactor.

1.8 grams of sodium silicate (25% w/w aqueous solution) were added and the mixture was stirred for 5 minutes. The pH was adjusted to 7.0 by the addition of 5 M HCl. The mixture was stirred for an additional 2 minutes, and 3 grams of poly(acrylamide-co-diallyldimethylammonium chloride (3% w/w aqueous solution)(PDAC) were added. The mixture was stirred for 5 minutes.

The process in the above paragraph (commencing with the addition of the sodium silicate) was repeated 49 times. Then, after 5 minutes of additional stirring, 1.8 grams of sodium silicate (25% w/w aqueous solution) was added. The pH was adjusted to 7.0 (using 5 M HCl) to produce a final dispersion which was kept stirred at 20 C for 12 hours. An assay indicated that the dispersion comprised 7.7% active ingredient.

Example #7

Silica Coating of Bifenthrin Using Non Ionic Polymer 2.1 grams of CTAC (29% w/w aqueous solution) were added to 125 grams of deionized water in a 1 liter flask, 125 grams of a 20% w/w aqueous dispersion of bifenthrin (also containing 0.5% W/w CTAC) were added. The mixture was homogenized using a Polytron PT 6100 Homoginizer and the resulting dispersion transferred to a Mettler Toledo LabMax Automatic Lab Reactor.

1.8 grams of sodium silicate (25% w/w aqueous solution) were added and the mixture was stirred for 5 minutes. The pH was adjusted to 3.0 by the addition of 5 M HCl. The mixture was stirred for an additional 2 minutes, and 3 grams of Celluol 24203 (a 3% w/w polyvinyl alcohol) added. The mixture was stirred for 5 minutes.

The process in the above paragraph (commencing with the addition of the sodium silicate) was repeated 49 times. Then, after 5 minutes of additional stirring, 1.8 grams of sodium silicate (25% w/w aqueous solution) was added. The pH was adjusted to 3.0 (using 5 M HCl) to produce a final dispersion which was kept stirred at 20 C (20° C.) for 12 hours. An assay indicated that the dispersion comprised 4.2% active ingredient.

Example #8

Silica Coating of Bifenthrin Using a Copolymer 2.1 grams of CTAC (29% w/w aqueous solution) were added to 125 grams of deionized water in a 1 liter flask. 125 grams of a 20% w/w aqueous dispersion of bifenthrin (also containing 0.5% CTAC) were added. The mixture was homogenized using a Polytron PT 6100 Homoginizer. An additional 75 grams of deionized water were added and the resulting dispersion transferred to a Mettler Toledo LabMax Automatic Lab Reactor.

1.8 grams of sodium silicate (25% w/w aqueous solution) were added and the mixture was stirred for 5 minutes. The pH was adjusted to 5.0 by the addition of 5 M HCl. The mixture was stirred for an additional 2 minutes, and 3 grams of Agrimer DA 102W (a 3% w/w aqueous suspension of vinyl pyrolidone/dimethylaminoethyl methacylate copolymer) added. The mixture was stirred for 5 minutes.

The process in the above paragraph (commencing with the addition of the sodium silicate) was repeated 49 times. Then, after 5 minutes of additional stirring, 1.8 grams of sodium silicate (25% w/w aqueous solution) was added. The pH was adjusted to 5.0 (using 5 M HCl) to produce a final dispersion which was kept stirred at 20 C for 12 hours. An assay indicated that the dispersion comprised 4.0% active ingredient.

Comparative Experiment A

Employing a sol-gel process of the type disclosed in U.S. Pat. No. 6,303,149, a core/shell composition of bifenthrin was prepared employing an aqueous phase comprising cetyltrimethylammonium chloride and an organic phase comprising tetraethoxysilane (TEOS) and bifenthrin technical in an aromatic organic solvent. The composition comprised 8.4% w/w of 96% bifenthrin technical.

Biological Testing

The residual activity of the above formulations on a porous surface (cement) against German Roaches was evaluated as follows:

Poured cement tiles were produced by mixing 1 part water with 3 parts dry cement mix powder (Quikrete or Sakrete). Once thoroughly mixed, the wet cement was poured directly into the "lid" side of plastic Petri dishes (100×20 mm). Enough wet cement was added to form a thin layer of cement 5-10 mm thick. The lids were agitated slightly to flatten out the cement and to prevent it from drying unevenly. The wet dishes were allowed to cure for 24 hours. The walls of the bottom of each Petri dish were coated with a 50/50 mixture of mineral oil and petroleum jelly to prevent the roaches from climbing up onto the untreated plastic portion of the Petri dishes, thereby escaping the treated cement surface.

The initial compositions above were diluted with distilled water to an application rate of 0.5 oz/gallon. A DeVilbis hand sprayer was used to spray the tiles, with treatments being applied at a rate ca. 0.005 mL/cm². The tiles were moved into a drying hood and held for 1-2 hours until completely dry. They were then used for initial (day 0) testing, or stored (at ambient humidity and at 68-75° F.) for residual evaluation.

German roaches were knocked down with carbon dioxide and transferred with featherweight forceps directly on to the treated surface. Ten roaches were added to each treated surface and the mineral oil/petroleum jelly coated Petri dish bottom was used as a cover. The percentage of roaches that were "knocked down" (which includes insects that were moribund—i.e, showed movement but failed to right themselves when turned over—or dead) was recorded at various time intervals.

The formulation of Comparative Experiment A showed no activity after 24 hours exposure after a 2 day residual treatment. In contrast, after a 28 day residual treatment, the formulations of Examples 6, 7 and 8 exhibited the following activity after 24 hour exposure:

| Example | Layer Coating | % Knockdown After 24 Hour Exposure |
|---------|---------------|-------------------------------------|
| Control | None          | 0                                   |
| 6       | PDAC          | 90                                  |
| 7       | PVA           | 100                                 |
| 8       | Agrimer       | 100                                 |

The above results show that the compositions of this invention exhibit unexpectedly prolonged activity of cement surfaces relative to the prior art process which also coats the bifenthrin with a silica shell.

While this invention has been shown and described with reference to preferred embodiments thereof, it will be understood by those skilled in the art that many alternatives, modifications and variations may be made thereto without departing from the spirit and scope of the invention. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference.

What is claimed is:

1. A process for coating solid benzoyl peroxide consisting of:
    (a) contacting, in an aqueous medium, the solid benzoyl peroxide with a cationic surfactant to obtain a dispersion of solid benzoyl peroxide having positive charges on its surface;
    (b) adding an aqueous solution of a metal oxide salt to said dispersion, under conditions wherein said metal oxide salt precipitates onto the benzoyl peroxide, and acidifying to thereby form benzoyl peroxide that has a metal oxide layer coated thereon;
        (b1) contacting, in an aqueous medium, the benzoyl peroxide coated with a metal oxide layer of the preceding step with a surface adhering additive being one or both of (i) a cationic polymer additive and (ii) a non-ionic additive, to obtain a dispersion of said coated solid benzoyl peroxide having an adhering additive on the surface thereof;
        (b2) bringing the dispersion obtained in step (b1) into contact with an aqueous solution of a metal oxide salt, under conditions wherein said metal oxide salt precipitates onto the surface of said coated solid benzoyl peroxide, and acidifying to thereby form a solid benzoyl peroxide that has a further metal oxide layer coated thereon;
    (c) repeating steps (b1) and (b2) at least 3 more times;
    (d) after completion of step (c), aging the metal oxide coating at a temperature ranging between 4° C. and 90° C. and at a pH of 3-9 to form a coated solid benzoyl peroxide, wherein no aging step is conducted between repeated coating steps, but only after completion of step c; and, optionally,
    (e) separating the coated, solid benzoyl peroxide from the aqueous medium and optionally rinsing and re-dispersing the coated, solid benzoyl peroxide in an aqueous medium.

2. The process of claim 1, wherein, in step (a), the solid, benzoyl peroxide is further contacted with an anionic additive.

3. The process of claim 1, wherein said cationic surfactant additive in step (a) is selected from the group consisting of monoalkylquaternary ammonium salts, dialkyl quaternary ammonium salts, and mixtures thereof.

4. Coated solid benzoyl peroxide obtained by the process according to claim 1.

5. The coated solid benzoyl peroxide of claim 4, wherein the weight ratio of the metal oxide to said solid benzoyl peroxide is in the range of 1:99 to 40:60.

6. A method for treating a surface condition in a subject, comprising topically administering onto the surface a composition comprising a coated solid benzoyl peroxide according to claim 4, wherein said surface condition is a disease or disorder selected from the group consisting of acne, infection, inflammation, pruritus, psoriasis, seborrhea, contact dermatitis, rosacea, and a combination thereof.

7. The method of claim 6, wherein said surface is skin or mucosal membrane.

8. The process of claim 1, wherein said metal oxide salt is an alkali metal salt of a metal oxide.

9. The process of claim 1, wherein the thickness of the metal oxide coating of benzoyl peroxide following step (d) is between 0.1-10 micron.

10. The process of claim 1, wherein said metal oxide is selected from silica, titania, alumina, zirconia, ZnO, and mixtures thereof.

11. The process of claim 10, wherein the metal oxide is silica.

* * * * *